US008854430B2

(12) United States Patent
Varslot et al.

(10) Patent No.: US 8,854,430 B2
(45) Date of Patent: Oct. 7, 2014

(54) IMAGE DATA PROCESSING

(75) Inventors: Trond Karsten Varslot, Bruce (AU);
Andrew Maurice Kingston, Griffith (AU); Adrian Paul Sheppard, Canberra (AU); Mark Alexander Knackstedt, Canberra (AU); Robert Martin Sok, Canberra (AU); Shane Jamie Latham, Canberra (AU)

(73) Assignee: FEI Company, Hillsboro, OR (US)

( * ) Notice: Subject to any disclaimer, the term of this patent is extended or adjusted under 35 U.S.C. 154(b) by 851 days.

(21) Appl. No.: 12/673,483

(22) PCT Filed: May 22, 2009

(86) PCT No.: PCT/AU2009/000641
§ 371 (c)(1),
(2), (4) Date: Apr. 14, 2011

(87) PCT Pub. No.: WO2009/140738
PCT Pub. Date: Nov. 26, 2009

(65) Prior Publication Data
US 2011/0181701 A1    Jul. 28, 2011

(30) Foreign Application Priority Data

May 23, 2008 (AU) ................................ 2008902590

(51) Int. Cl.
*H04N 13/02* (2006.01)
*G06T 7/00* (2006.01)

(52) U.S. Cl.
CPC ..... *G06T 7/0024* (2013.01); *G06T 2207/20016* (2013.01); *G06T 2207/10081* (2013.01); *G06T 2207/30108* (2013.01)

USPC ........................................................... 348/46

(58) Field of Classification Search
USPC ........................................................... 348/46
See application file for complete search history.

(56) References Cited

U.S. PATENT DOCUMENTS

| 5,647,360 | A | 7/1997 | Bani-Hashemi et al. |
|---|---|---|---|
| 6,283,918 | B1 | 9/2001 | Kanda et al. |
| 6,359,617 | B1 | 3/2002 | Xiong |
| 6,373,998 | B2 | 4/2002 | Thirion et al. |
| 6,675,189 | B2 | 1/2004 | Rehg et al. |
| 6,765,570 | B1* | 7/2004 | Cheung et al. ................. 345/420 |
| 7,234,937 | B2 | 6/2007 | Sachdeva et al. |
| 2001/0021263 | A1 | 9/2001 | Oosawa |
| 2001/0032051 | A1* | 10/2001 | Grismore et al. ................ 702/16 |

(Continued)

FOREIGN PATENT DOCUMENTS

WO    WO 2006/135024  A1    12/2006

OTHER PUBLICATIONS

Kaufman, Voxels as a Computational Representation of Geomery, 1996, State University of New York at Stony Brook, pp. 1-45.*

(Continued)

*Primary Examiner* — Sath V Perungavoor
*Assistant Examiner* — Peter D Le
(74) *Attorney, Agent, or Firm* — Fenwick & West LLP

(57) ABSTRACT

A method for processing image data of a sample is disclosed. The method comprises registering a first and a second images of at least partially overlapping spatial regions of the sample and processing data from the registered images to obtain integrated image data comprising information about the sample, said information being additional to that available from said first and second images.

6 Claims, 23 Drawing Sheets

(56) References Cited

U.S. PATENT DOCUMENTS

| | | | |
|---|---|---|---|
| 2003/0099388 | A1 | 5/2003 | Doi et al. |
| 2005/0035296 | A1* | 2/2005 | Kojima et al. ............ 250/363.03 |
| 2005/0283066 | A1 | 12/2005 | Yamada |
| 2006/0002630 | A1* | 1/2006 | Fu et al. ......................... 382/294 |
| 2006/0062442 | A1* | 3/2006 | Arnaud et al. ................. 382/128 |
| 2006/0116575 | A1* | 6/2006 | Willis ............................. 600/434 |
| 2007/0127845 | A1* | 6/2007 | Fu et al. ......................... 382/294 |
| 2007/0253618 | A1* | 11/2007 | Kim et al. ...................... 382/154 |
| 2008/0095421 | A1 | 4/2008 | Sun et al. |
| 2008/0260221 | A1* | 10/2008 | Unal et al. ..................... 382/128 |
| 2008/0300484 | A1* | 12/2008 | Wang et al. ................... 600/431 |
| 2009/0288880 | A1 | 11/2009 | Wojcik et al. |
| 2010/0027861 | A1* | 2/2010 | Shekhar et al. ............... 382/131 |
| 2011/0004447 | A1* | 1/2011 | Hurley et al. ....................... 703/1 |
| 2011/0103657 | A1* | 5/2011 | Kang et al. .................... 382/128 |

OTHER PUBLICATIONS

Laurent et al., Comparison of Parallel Reconstruction Algorithms for 3D X-Ray Tomography on MIMD Compters, Jan. 26, 2008; TIMC-IMAG Laboratory, pp. 1-12.*

DBX, Bone Graft Substitute, 2007, DBX, pp. 1-8.*

PCT International Search Report, PCT Application No. PCT/AU2009/000641, Jul. 13, 2009, 5 pages.

Arns, C.H. et al., "Accurate Estimation of Transport Properties from Microtomographic Images," Geophysical Research Letters, Sep. 1, 2001, pp. 3361-3364, vol. 28, No. 17.

Arns, C.H. et al., "Computation of Linear Elastic Properties from Microtomographic Images: Methodology and Agreement Between Theory and Experiment," Geophysics, Sep.-Oct. 2002, pp. 1396-1405, vol. 67, No. 5.

Arns, C.H. et al., "Digital Core Laboratory: Petrophysical Analysis from 3D Imaging of Reservoir Core Fragments," Petrophysics, Aug. 2005, pp. 260-277, vol. 46, No. 4.

Arns, C.H. et al., "NMR Petrophysical Predictions on Digitized Core Images," SPWLA 46$^{th}$ Annual Logging Symposium, Jun. 26-29, 2005, pp. 1-16.

Arns, C.H. et al., "Virtual Permeametry on Microtomographic Images," Journal of Petroleum Science and Engineering, 2004, pp. 41-46, No. 45.

Baechle, G.T. et al., "Effect of Spherical Pore Shapes on Acoustic Properties in Carbonates," AAPG Annual Convention, Long Beach, CA, 2007, 22 pages.

Baechle, G.T. et al., "The Role of Macroporosity and Microporosity in Constraining Uncertainties and in Relating Velocity to Permeability in Carbonate Rocks," SEG Int'l Exposition and 74$^{th}$ Annual Meeting, Denver, Colorado, Oct. 10-15, 2004, 4 pages.

Behbahani, H. et al., "Analysis of Imbibition in Mixed-Wet Rocks Using Power-Scale Modeling," Presented at SPE Annual Technical Conference and Exhibition, Houston, Sep. 26-29, 2004, pp. 466-473.

Blunt, M.J. et al., "Detailed Physics, Predictive Capabilities and Macroscopic Consequences for Pore-Network Models of Multiphase Flow," Advances in Water Resources, 2002, pp. 1069-1089, vol. 25.

Bohn, R.B. et al., "User Manual for Finite Element and Finite Difference Programs: A Parallel Version of NIST IR 6269," National Institute of Standards and Technology, U.S. Department of Commerce, Jun. 19, 2003, 277 pages.

Cantrell, D.L. et al., "Microporosity in Arab Formation Carbonates, Saudi Arabia," GeoArabia, 1999, pp. 129-154, vol. 4, No. 2.

Clerke, E.A., "Permeability, Relative Permeability, Microscopic Displacement Efficiency, and Pore Geometry of M_1 Bimodal Pore Systems in Arab D Limestone" Presented at SPE Middle East Oil and Gas Show and Conference, Bahrain, Mar. 11-14, 2007, Published Sep. 2009 SPE Journal, pp. 524-531.

Dautriat, J. et al., "Laboratory Determination of Stress-Path Dependency of Directional Permeabilities of Estaillades Limestone," Presented at the International Symposium of the Society of Core Analysts, Abu Dhabi, UAE, Oct. 29-Nov. 2, 2008, pp. 1-12.

Ehrenberg, S.N. et al., "Porosity-Permeability Relationships in Miocene Carbonate Platforms and Slopes Seaward of the Great Barrier Reef, Australia (ODP Leg 194, Mario Plateau)," Sedimentology, 2006, pp. 1289-1318, vol. 53.

Graue, A. et al., "Alteration of Wettability and Wettability Heterogeneity," Journal of Petroleum Science and Engineering, 2002, pp. 3-17, vol. 33.

Knackstedt, M.A. et al., "Archie's Exponents in Complex Lithologies Derived from 3D Digital Core Analysis," SPWLA 48$^{th}$ Annual Logging Symposium, Jun. 3-6, 2007, pp. 1-16.

Latham, S. et al., "Image Registration: Enhancing and Calibrating X-Ray Micro-CT Imaging," Presented at the International Symposium of the Society of Core Analysts, Abu Dhabi, Oct. 29-Nov. 2, 2008, pp. 1-12.

Lucia, F.J., "Petrophysical Parameters Estimated from Visual Descriptions of Carbonated Rocks: A Field Classification of Carbonate Pore Space," Journal of Petroleum Technology, Mar. 1983, pp. 629-637.

Morrow, N.R., "Wettability and Its Effect on Oil Recovery," Journal of Petroleum Technology, Dec. 1990, pp. 1476-1484.

Morrow, N.R. et al., "Recovery of Oil by Spontaneous Imbibition," Current Opinion in Colloid & Interface Science, 2001, pp. 321-337, vol. 6.

PCT International Preliminary Report on Patentability, PCT/AU2009/000641, Nov. 23, 2010, 7 pages.

Prodanovic, M. et al., "3D Image-Based Characterization of Fluid Displacement in a Berea Core," Advances in Water Resources, 2007, pp. 214-226, vol. 30.

Ramakrishnan, T.S. et al., "A Model-Based Interpretation Methodology for Evaluating Carbonate Reservoirs," Presented at 2001 SPE Annual Technical Conference and Exhibition, New Orleans, Louisiana, Sep. 30-Oct. 3, 2001, pp. 1-15.

Sakellariou, A. et al., "An X-Ray Tomography Facility for Quantitative Prediction of Mechanical and Transport Properties in Geological, Biological and Synthetic Systems," Developments in X-Ray Tomography IV, Proc. of SPIE, 2004, pp. 473-484, vol. 5535.

Sakellariou, A. et al., "X-Ray Tomography for Mesoscale Physics Applications," Physica A, 2004, pp. 152-158, vol. 339.

Seright, R.S. et al., "Characterizing Disproportionate Permeability Reduction Using Synchrotron X-Ray Computed Microtomography," SPE Reservoir Evaluation & Engineering, Oct. 2002, pp. 355-364.

Sheppard, A.P. et al., "Techniques for Image Enhancement and Segmentation of Tomographic Images of Porous Materials," Physica A, 2004, pp. 145-151, vol. 339.

Sok, R.M. et al., "Estimation of Petrophysical Parameters from 3D Images of Carbonate Core," Presented at SPWLA Middle East Regional Symposium, Abu Dhabi, UAE, Apr. 15-19, 2007, pp. 1-15.

Nakano, T. et al., "Observation and Analysis of Internal Structure of Rock Using X-Ray CT," Jour. Geol. Soc. Japan, May 2000, pp. 363-378, vol. 106, No. 5. (with English abstract).

Chinese Third Office Action, Chinese Application No. 200980118140.6, Oct. 17, 2013, 16 pages.

* cited by examiner

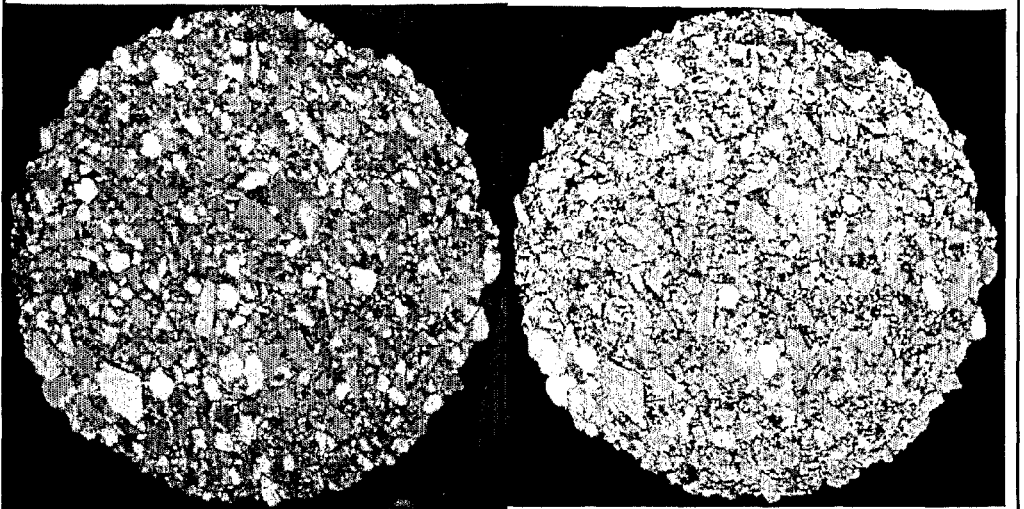
Fig. 4A — Optical microscope image detailing mineralogy
Fig. 4B — Coregistered slice from 3D tomogram
Fig. 5 — SEM: 50 nm resolution
Fig. 6 — Registered slice from Tomography Data 2.5 micron voxels (50x poorer resolution)

SEM image of a regular square grid used to determine distortion in the image.

Solid dark box: center portion of a grid image, used as a stencil.
Light dashed box: a location where the stencil pattern is repeated.

Five correlation maxima closest to the origin (black dots), and their relationship to the grid principal axes u and v.

Two SEM images merged without de-warping

Same images merged after de-warping

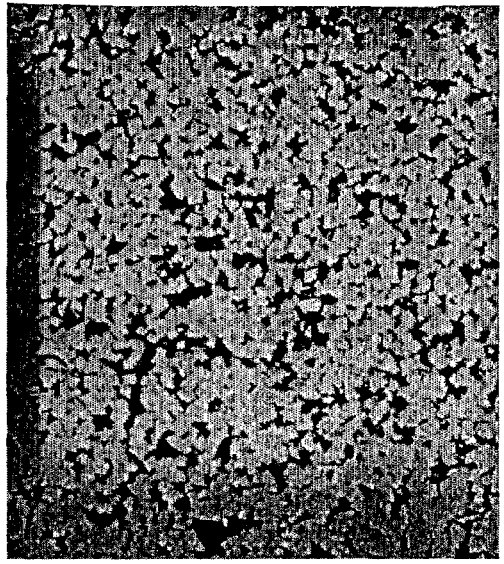
Fig. 13 — Dry image
Fig. 14 — After fluid uptake
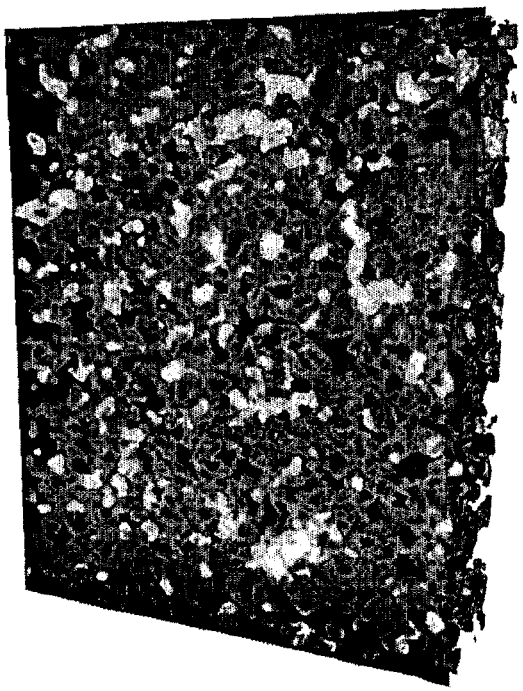
Fig. 15

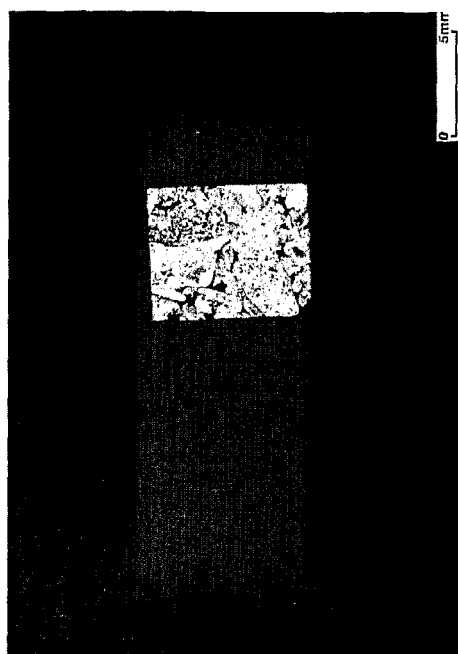
Fig. 33

IMAGE DATA PROCESSING

FIELD OF INVENTION

Methods and systems are described that relate to imaging techniques and, in particular, to processing image data to gain an understanding of a property of a physical sample from which the image data is taken.

DESCRIPTION OF BACKGROUND ART

Image analysis of core materials in the geological sciences has been primarily the discipline of the sedimentologists and the petrographers. Two dimensional (2D) image data from optical and scanning electron microscopy (SEM) techniques have been utilized to estimate porosity, pore size, grain size, flow units, permeability, velocity and compressibility. Conventional petrographic techniques allow the identification of mineral phase information and origins of mineral phases (e.g., detrital or authigenic). Length scales down to nanometers can be probed.

On the other hand, X-ray micro computed tomography (CT), with its ability to generate detailed three dimensional (3D) images of pore structure on the micron scale, has recently become accepted as a useful complement to the well established 2D microscopic techniques. The availability of high quality "turn-key" tomographic systems has recently facilitated the rapid increase in the use of these systems. These systems allow one to obtain pore/grain scale information on porous materials in three dimensions. Unfortunately, the conventional micro-CT imaging gives poor mineral discrimination and is limited to spatial resolutions of about 1 micron.

Increasing levels of attention have recently been focussed on the characterization and measurement of properties at the pore/grain/clay scale of core materials; understanding properties at this scale is crucial to applications in the oil and gas industries. Analyses of core samples are used to generate key petrophysical and multiphase flow properties. These properties are crucial to reducing the high financial risk that petroleum companies face in finding, bringing to production and operating oil and gas fields. Compared to the cost of bringing a new field into production or the potential profit from extending the life of an existing field, the cost of the analyses themselves is low. Core analysis remains the industry standard data for estimating reserves and predicting recovery rates. This is despite the fact that core analysis may often provide conflicting data and data which is difficult to interpret and difficult to reproduce. Such difficulties are at least partially due to the complex interfacial phenomena that need to be addressed at a fundamental level for better understanding of multiphase flow properties.

Measurements obtained in conventional multiphase flow experiments within core laboratories are used to study both the pore scale structure of the rock and the interfacial properties of the fluid/fluid and fluid/rock interactions. There is an enormous interest in the development of rules and methods for modelling pore level displacements that apply to multiphase flow. Pore network models which include rules for occupancy of fluids in individual pores under different wettability scenarios (water wet, mixed wet large/small) are being developed in an attempt to improve understanding of multiphase flow properties in real porous materials (see e.g., Morrow & Mason, "*Recovery of Oil by spontaneous imbibition*", Current Opinion in Colloid & Interface Science, Vol. 6, pp. 321-337 (2001) and H. Behbahani and M. Blunt, "*Analysis of Imbibition in mixed wet rocks using pore scale modelling*", SPE 90132, presented at SPE Annual Technical Conference, Houston, 2004). To date, no methodology has allowed the direct calibration of the pore network model descriptions of the different fluid phases to experimental pore level information on the distribution of the fluid phases under realistic wettability conditions. Therefore, no direct pore-level calibration of pore scale modelling has been possible.

It has been demonstrated that direct simulation on CT images can be used to predict single phase properties of porous materials; e.g. permeability, conductivity and mercury injection capillary pressure curves (see e.g. "*Digital core laboratory: Petrophysical analysis from 3D imaging of reservoir core fragments*", C. H. Arns, F. Bauget, A. Ghous, A. Sakellariou, T. J. Senden, A. P. Sheppard, R. M. Sok, W. V. Pinczewski, J. Kelly, and M. A. Knackstedt, *Petrophysics*, 46(4), 260-277, 2005.)

Previous studies have demonstrated the ability to identify the pore scale distribution of fluids in 3D on the basis of micro-CT imaging experiments (see Seright et al., "*Characterizing disproportionate permeability reduction using synchrotron X-ray computed tomography*", SPE Reservoir Evaluation and Engineering, October 2002, pp. 355-364). However these studies were severely hampered by the need to flood the core sample under investigation, without removing the sample from the X-ray CT beam line. This limits experiments undertaken at the pore scale in 3D to simple flooding experiments.

Moreover, these experiments have been limited by the need to maintain micron-perfect positioning of the core material over long acquisition times. Thus, an experiment involving significant equilibration times (e.g. steady state relative permeability measurements under reservoir conditions, ageing of a core in native crude and brine, porous plate flooding etc.) may require the sample to remain on the CT equipment for weeks or even months.

SUMMARY

It is the object of the present invention to substantially overcome, or at least ameliorate, one or more disadvantages of the known arrangements, or to provide a useful alternative.

According to a first aspect of the present disclosure, there is provided method for processing image data of a sample, the method comprising registering a first and a second images of at least partially overlapping spatial regions of the sample; and processing data from the registered images to obtain integrated image data comprising information about the sample, said information being additional to that available from said first and second images.

According to a second aspect of the present disclosure, there is provided a computer program executable to effect the steps of the method of the first aspect.

According to a third aspect of the present disclosure, there is provided a computer program product having a computer readable medium, wherein the computer readable medium comprises a computer program of the second aspect.

According to a further aspect of the present disclosure, there is provided an electronic system for processing image data of a sample comprising:

imaging means arranged for acquiring a first and a second images of at least partially overlapping spatial regions of the sample;

a storage device arranged for storing the acquired images; and at least one microprocessors arranged for retrieving and registering data of the acquired images to obtain integrated image data, the integrated image data comprising information about the sample, said information being additional to that available from said first and second images.

Other aspects of the present disclosure are also disclosed.

BRIEF DESCRIPTION OF THE DRAWINGS

One or more embodiments of the invention will now be described with reference to the following drawings, in which:

FIG. 4A and FIG. 4B show a 2D optical microscopy image and a 3D tomographic image, respectively.

FIG. 5 and FIG. 6 show a 2D microscopy image and a registered 3D tomographic image, respectively, the images having substantially different spatial resolution.

FIG. 13 shows a sample before fluid intake and

FIG. 14 shows a sample after fluid intake.

FIG. 15 is a snapshot from a movie showing fluid distribution within a sample, the fluid distribution being derived by aligning 3D images.

FIG. 16A shows 3D phase distribution, while FIG. 16B shows a correlation between pore size distribution and fluid content.

FIG. 33 shows an application of registration of 3D images of multiple resolutions.

DETAILED DESCRIPTION

FIGS. 1 to 35 show various aspects of the disclosed method for processing the data obtained by integrating the registered 2D and 3D images and practical applications enabled by such processing.

A. Hardware Implementation

Figure 36A:
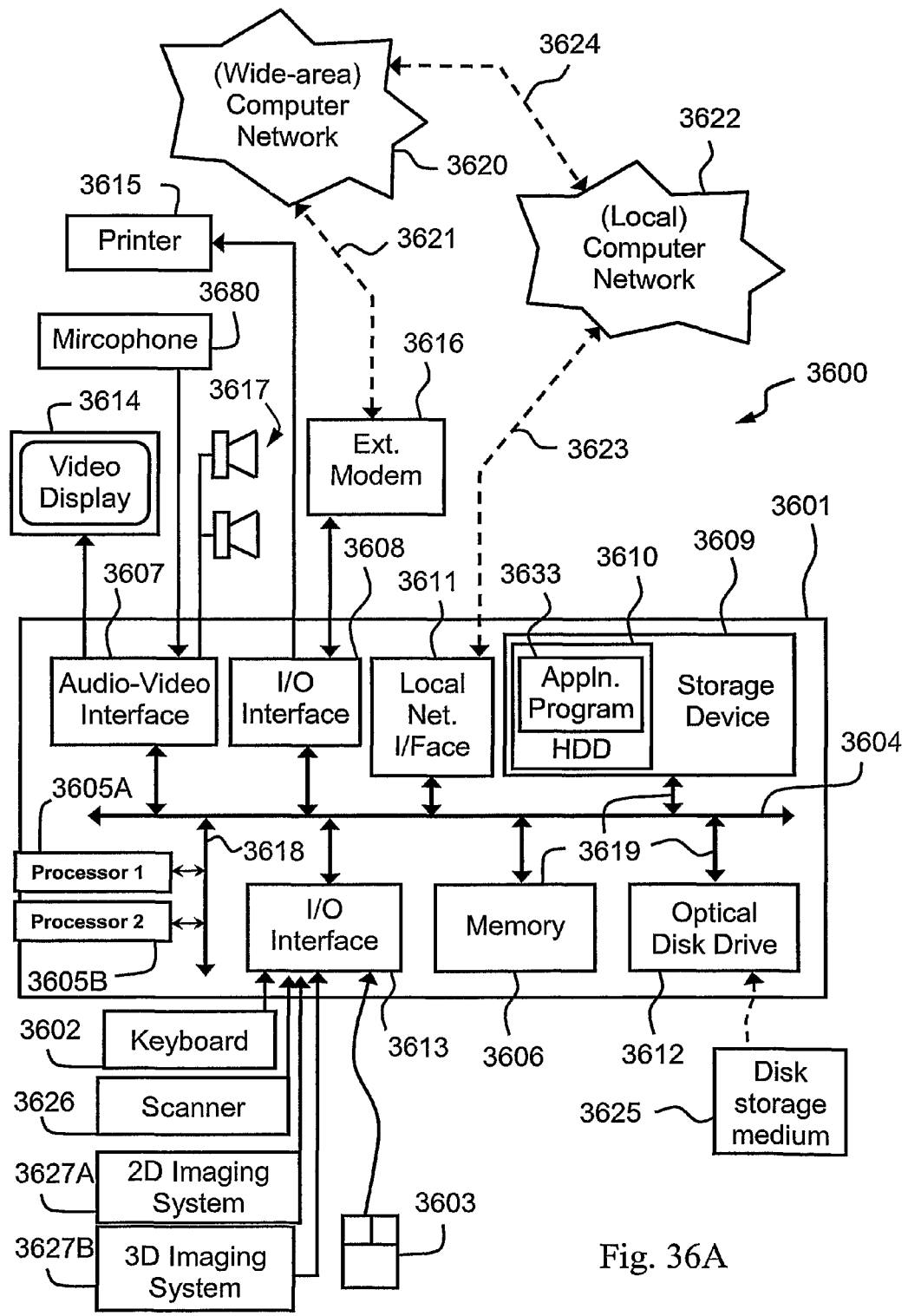
FIGS. 36A and 36B form a schematic block diagram of a general purpose computer system upon which the arrangements described can be practiced.
Figure 36B:
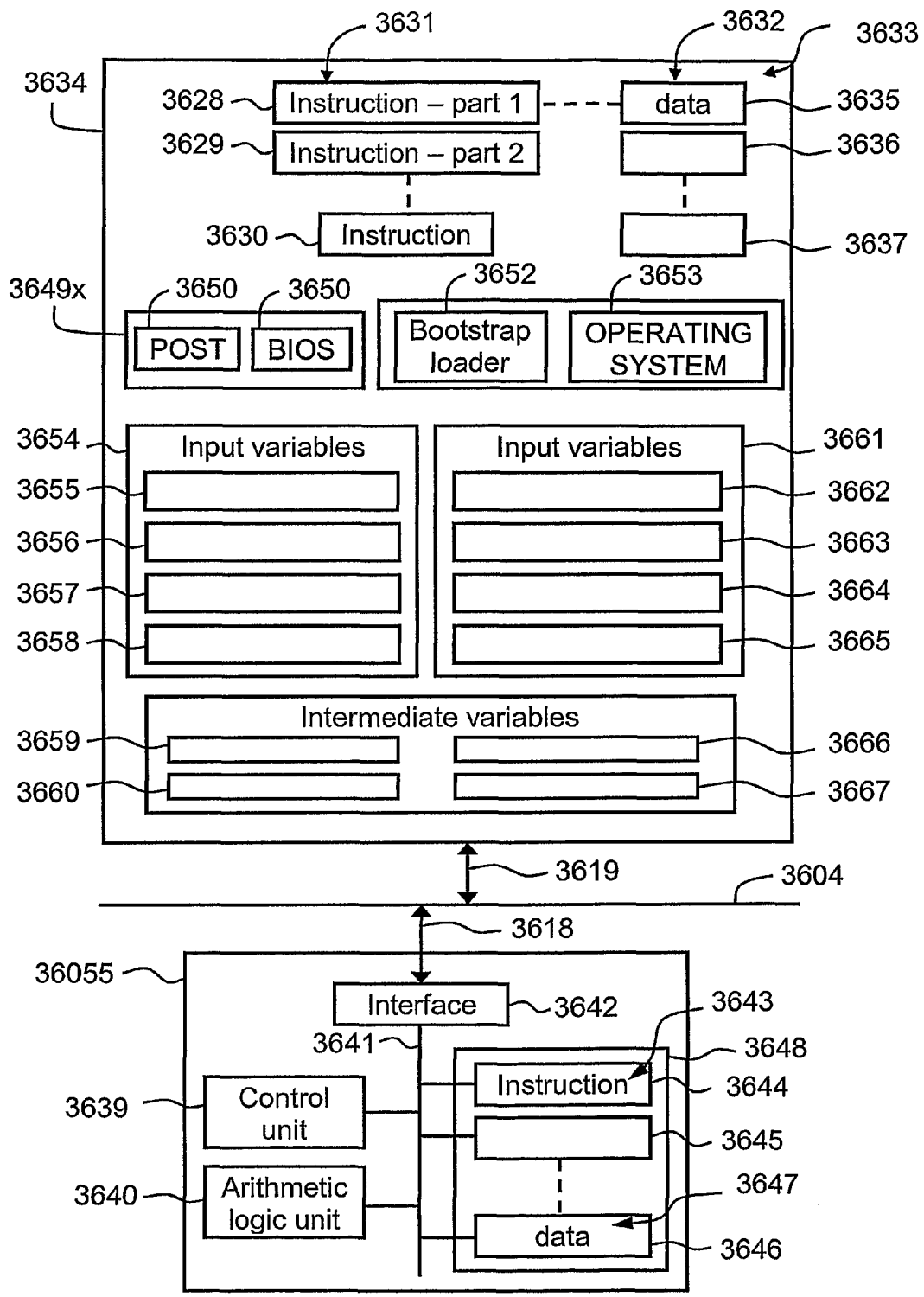

FIGS. 36A and 36B collectively form a schematic block diagram of a general purpose computer system 3600, upon which the various arrangements described can be practiced.

As seen in FIG. 36A, the computer system 3600 is formed by a computer module 3601, input devices such as a keyboard 3602, a mouse pointer device 3603, a scanner 3626 and a microphone 3680, and output devices including a printer 3615, a display device 3614 and loudspeakers 3617. One or more imaging devices 3627 can also be directly connected to the computer module 3601. These devices provide the image data to be processed by the method discussed thereafter.

An external Modulator-Demodulator (Modem) transceiver device 3616 may be used by the computer module 3601 for communicating to and from a communications network 3620 via a connection 3621. The network 3620 may be a wide-area network (WAN), such as the Internet or a private WAN. Where the connection 3621 is a telephone line, the modem 3616 may be a traditional "dial-up" modem. Alternatively, where the connection 3621 is a high capacity (eg: cable) connection, the modem 3616 may be a broadband modem. A wireless modem may also be used for wireless connection to the network 3620.

The computer module 3601 typically includes at least one processor unit and a memory unit 3606 for example formed from semiconductor random access memory (RAM) and semiconductor read only memory (ROM). The computer system shown in FIG. 36A comprises two processors 3605A and 3605B, which enable the parallel processing implemented in at least some of the steps of the method described below. The module 3601 also includes an number of input/output (I/O) interfaces including an audio-video interface 3607 that couples to the video display 3614, loudspeakers 3617 and microphone 3680, an I/O interface 3613 for the keyboard 3602, mouse 3603, scanner 3626, imaging device 3627 and optionally a joystick (not illustrated), and an interface 3608 for the external modem 3616 and printer 3615. In some implementations, the modem 3616 may be incorporated within the computer module 3601, for example within the interface 3608. The computer module 3601 also has a local network interface 3611 which, via a connection 3623, permits coupling of the computer system 3600 to a local computer network 3622, known as a Local Area Network (LAN). As also illustrated, the local network 3622 may also couple to the wide network 3620 via a connection 3624, which would typically include a so-called "firewall" device or device of similar functionality. The interface 3611 may be formed by an Ethernet™ circuit card, a Bluetooth™ wireless arrangement or an IEEE 802.11 wireless arrangement.

The interfaces 3608 and 3613 may afford either or both of serial and parallel connectivity, the former typically being implemented according to the Universal Serial Bus (USB) standards and having corresponding USB connectors (not illustrated). Storage devices 3609 are provided and typically include a hard disk drive (HDD) 3610. Other storage devices such as a floppy disk drive and a magnetic tape drive (not illustrated) may also be used. An optical disk drive 3612 is typically provided to act as a non-volatile source of data. Portable memory devices, such optical disks (eg: CD-ROM, DVD), USB-RAM, and floppy disks for example may then be used as appropriate sources of data to the system 3600.

The components 3605 to 3613 of the computer module 3601 typically communicate via an interconnected bus 3604 and in a manner which results in a conventional mode of operation of the computer system 3600 known to those in the relevant art. Examples of computers on which the described arrangements can be practised include IBM-PCs and compatibles, Sun Sparcstations, Apple Mac™ or alike computer systems evolved therefrom.

Figure 1:
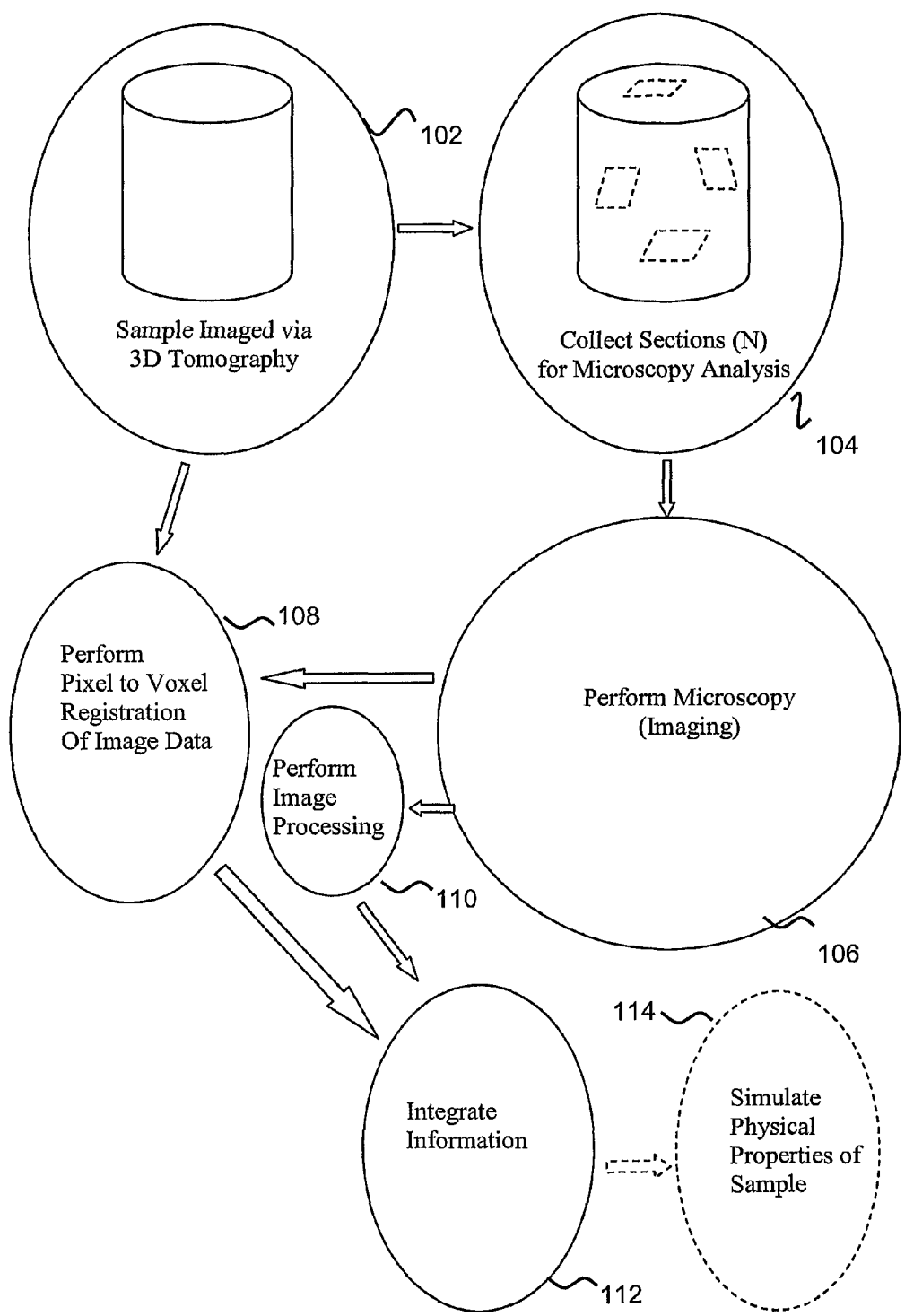
FIG. 1 shows a schematic flow diagram of the method according one embodiment of the invention, the method being related to registering 2D and 3D images and subsequently integrating the information from both images.
Figure 12:
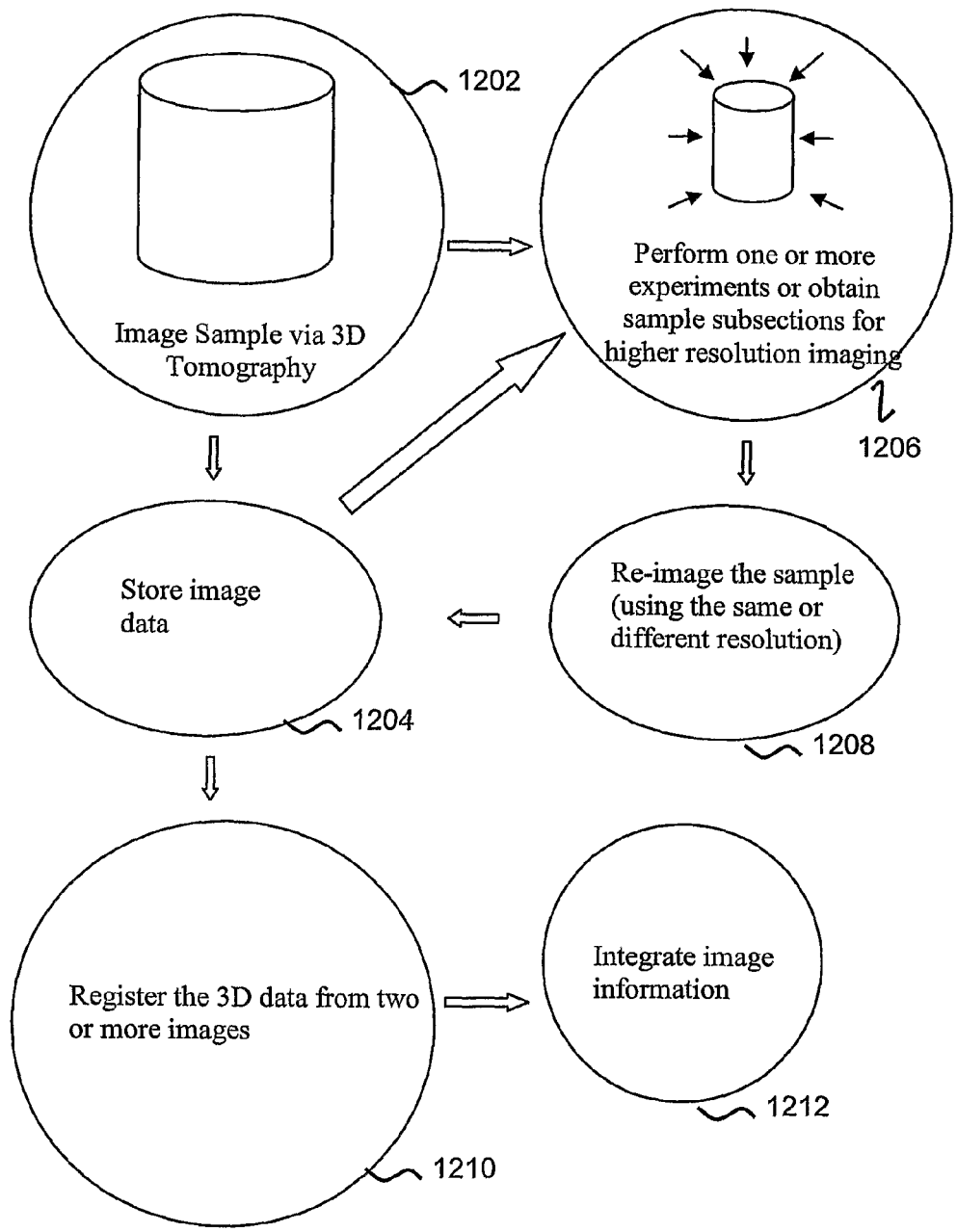
FIG. 12 shows a schematic flow diagram of the method according to a second embodiment of the invention, the method being related to aligning 3D with 3D images and subsequently integrating information from both images.
Figure 19:
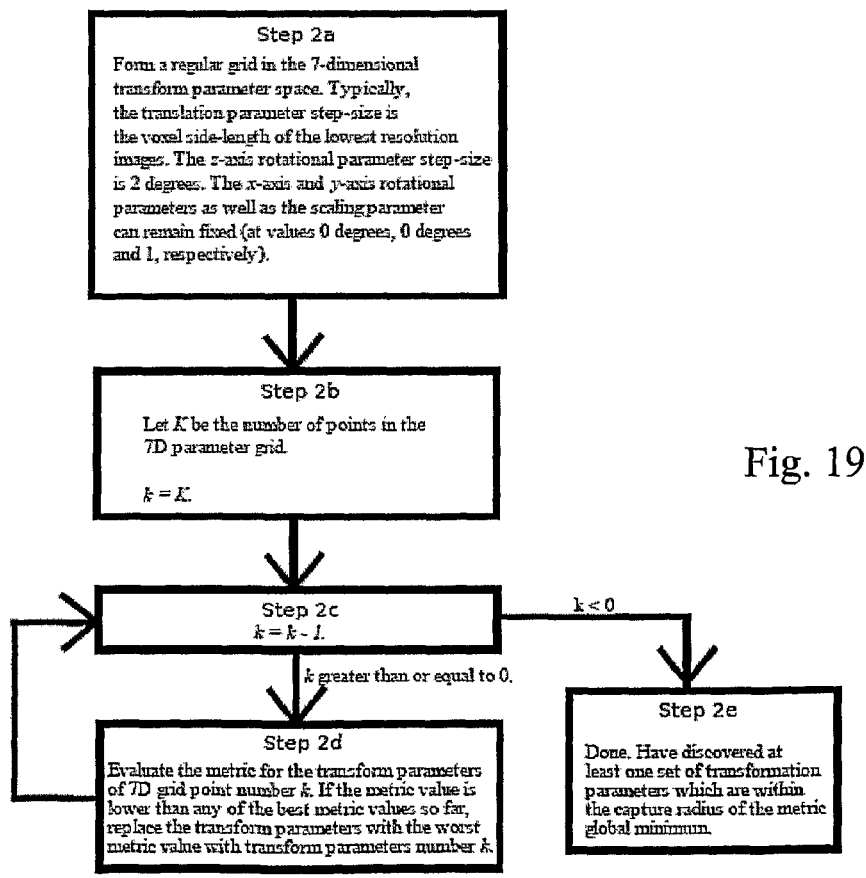
FIG. 19 shows details of the flow diagram of step 2 of the algorithms shown in FIGS. 17 and 18.
Figure 17:
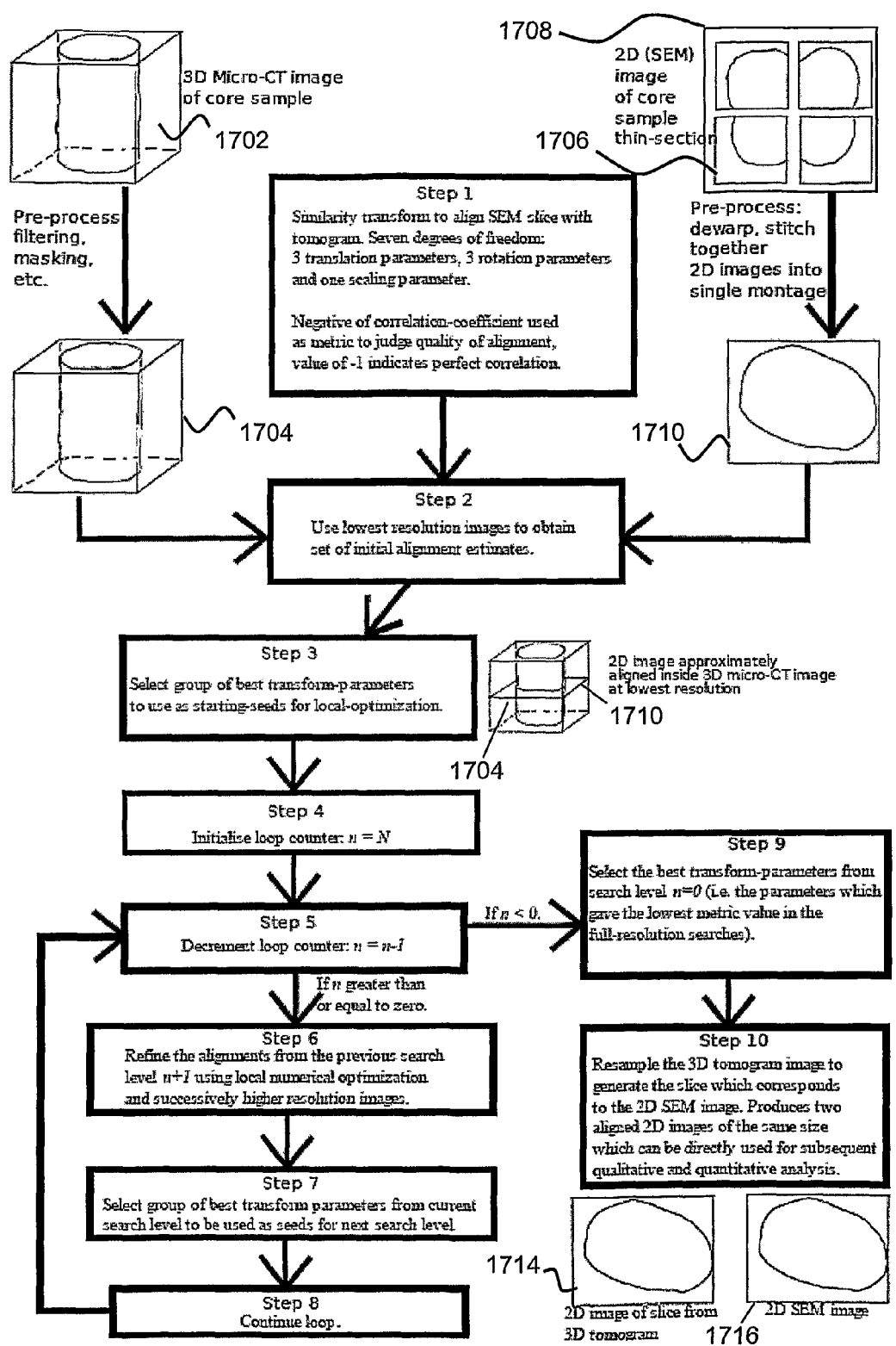
FIG. 17 shows an algorithm of the computational process associated with the first embodiment of the invention.
Figure 18:
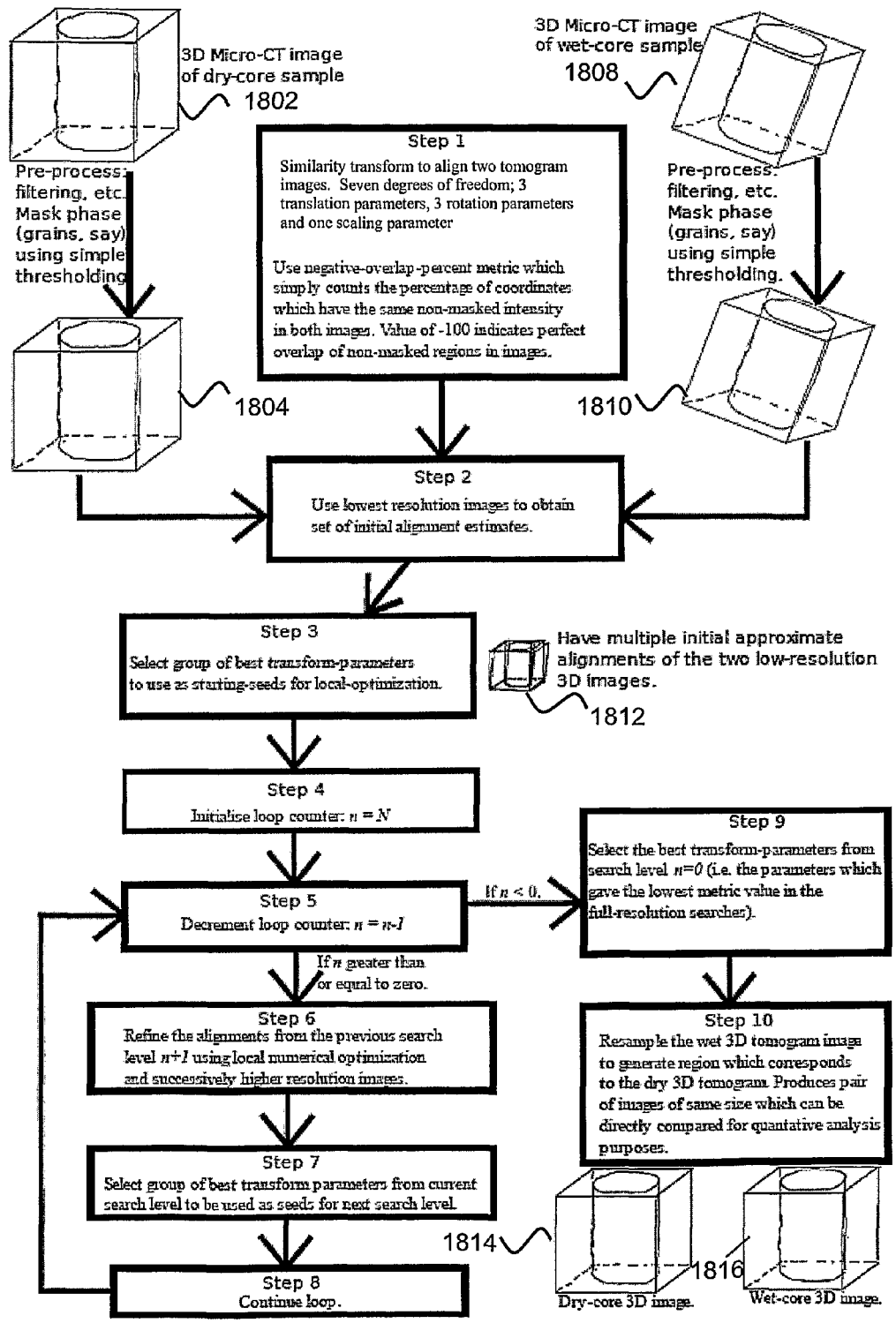
FIG. 18 shows an algorithm of the computational process associated with the second embodiment of the invention.

The discussed image processing method may be implemented using the computer system 3600 wherein the steps of FIGS. 1 and 12 and the computational algorithms of FIGS. 17 to 19, to be described, may be implemented as one or more software application programs 3633 executable within the computer system 3600. In particular, the steps of the discussed method are effected by instructions 3631 in the software 3633 that are carried out within the computer system 3600. The software instructions 3631 may be formed as one or more code modules, each for performing one or more particular tasks. The software may also be divided into two separate parts, in which a first part and the corresponding code modules performs the steps of the method and a second part and the corresponding code modules manage a user interface between the first part and the user.

The software 3633 is generally loaded into the computer system 3600 from a computer readable medium, and is then typically stored in the HDD 3610, as illustrated in FIG. 36A, or the memory 3606, after which the software 3633 can be executed by the computer system 3600. In some instances, the application programs 3633 may be supplied to the user encoded on one or more CD-ROM 3625 and read via the corresponding drive 3612 prior to storage in the memory 3610 or 3606. Alternatively the software 3633 may be read by the computer system 3600 from the networks 3620 or 3622 or loaded into the computer system 3600 from other computer readable media. Computer readable storage media refers to any storage medium that participates in providing instructions and/or data to the computer system 3600 for execution and/or processing. Examples of such storage media include floppy disks, magnetic tape, CD-ROM, a hard disk drive, a ROM or integrated circuit, USB memory, a magneto-optical disk, or a computer readable card such as a PCMCIA card and the like, whether or not such devices are internal or external of the computer module 3601. Examples of computer readable transmission media that may also participate in the provision of software, application programs, instructions and/or data to the computer module 3601 include radio or infra-red transmission channels as well as a network connection to another computer or networked device, and the Internet or Intranets including e-mail transmissions and information recorded on Websites and the like.

The second part of the application programs 3633 and the corresponding code modules mentioned above may be executed to implement one or more graphical user interfaces (GUIs) to be rendered or otherwise represented upon the display 3614. Through manipulation of typically the keyboard 3602 and the mouse 3603, a user of the computer system 3600 and the application may manipulate the interface in a functionally adaptable manner to provide controlling commands and/or input to the applications associated with the GUI(s). Other forms of functionally adaptable user interfaces may also be implemented, such as an audio interface utilizing speech prompts output via the loudspeakers 3617 and user voice commands input via the microphone 3680.

FIG. 36B is a detailed schematic block diagram of one of the processors 3605A or 3605B and a "memory" 3634. The memory 3634 represents a logical aggregation of all the memory devices (including the HDD 3610 and semiconductor memory 3606) that can be accessed by the computer module 3601 in FIG. 36A.

When the computer module 3601 is initially powered up, a power-on self-test (POST) program 3650 executes. The POST program 3650 is typically stored in a ROM 3649 of the semiconductor memory 3606. A program permanently stored in a hardware device such as the ROM 3649 is sometimes referred to as firmware. The POST program 3650 examines hardware within the computer module 3601 to ensure proper functioning, and typically checks a respective one of processors 3605A or 3605B, the memory (3609, 3606), and a basic input-output systems software (BIOS) module 3651, also typically stored in the ROM 3649, for correct operation. Once the POST program 3650 has run successfully, the BIOS 3651 activates the hard disk drive 3610. Activation of the hard disk drive 3610 causes a bootstrap loader program 3652 that is resident on the hard disk drive 3610 to execute via a respective one of processors 3605A or 3605B. This loads an operating system 3653 into the RAM memory 3606 upon which the operating system 3653 commences operation. The operating system 3653 is a system level application, executable by a respective one of processors 3605A or 3605, to fulfil various high level functions, including processor management, memory management, device management, storage management, software application interface, and generic user interface.

The operating system 3653 manages the memory (3609, 3606) in order to ensure that each process or application running on the computer module 3601 has sufficient memory in which to execute without colliding with memory allocated to another process. Furthermore, the different types of memory available in the system 3600 must be used properly so that each process can run effectively. Accordingly, the aggregated memory 3634 is not intended to illustrate how particular segments of memory are allocated (unless otherwise stated), but rather to provide a general view of the memory accessible by the computer system 3600 and how such is used.

Each of the processors 3605A and 3605B includes a number of functional modules including a control unit 3639, an arithmetic logic unit (ALU) 3640, and a local or internal memory 3648, sometimes called a cache memory. The cache memory 3648 typically includes a number of storage registers 3644-3646 in a register section. One or more internal buses 3641 functionally interconnect these functional modules. Each of the processors 3605A or 3605B typically also has one or more interfaces 3642 for communicating with external devices via the system bus 3604, using a connection 3618.

The application program 3633 includes a sequence of instructions 3631 that may include conditional branch and loop instructions. The program 3633 may also include data 3632 which is used in execution of the program 3633. The instructions 3631 and the data 3632 are stored in memory locations 3628-3630 and 3635-3637 respectively. Depending upon the relative size of the instructions 3631 and the memory locations 3628-3630, a particular instruction may be stored in a single memory location as depicted by the instruction shown in the memory location 3630. Alternately, an instruction may be segmented into a number of parts each of which is stored in a separate memory location, as depicted by the instruction segments shown in the memory locations 3628-3629.

In general, the processors 3605A and 3605B are given a set of instructions which are executed therein. The processors then wait for a subsequent input, to which it reacts to by executing another set of instructions. Each input may be provided from one or more of a number of sources, including data generated by one or more of the input devices 3602, 3603, data received from an external source across one of the networks 3620, 3622, data retrieved from one of the storage devices 3606, 3609 or data retrieved from a storage medium 3625 inserted into the corresponding reader 3612. The execution of a set of the instructions may in some cases result in output of data. Execution may also involve storing data or variables to the memory 3634.

The computational arrangements disclosed later in the text use input variables 3654, that are stored in the memory 3634 in corresponding memory locations 3655-3658. The performed calculations produce output variables 3661 that are stored in the memory 3634 in corresponding memory locations 3662-3665. Intermediate variables may be stored in memory locations 3659, 3660, 3666 and 3667.

The register section 3644-3646, the arithmetic logic unit (ALU) 3640, and the control unit 3639 of the operational one or more processors 3605A and/or 3605B work together to perform sequences of micro-operations needed to perform "fetch, decode, and execute" cycles for every instruction in the instruction set making up the program 3633. Each fetch, decode, and execute cycle comprises:

(a) a fetch operation, which fetches or reads an instruction 3631 from a memory location 3628;

(b) a decode operation in which the control unit 3639 determines which instruction has been fetched; and (c) an execute operation in which the control unit 3639 and/or the ALU 3640 execute the instruction.

Thereafter, a further fetch, decode, and execute cycle for the next instruction may be executed. Similarly, a store cycle may be performed by which the control unit 3639 stores or writes a value to a memory location 3632.

Each step or sub-process in the algorithms of FIGS. 17 to 19 is associated with one or more segments of the program 3633, and is performed by the register section 3644-3647, the ALU 3640, and the control unit 3639 in the processor 3605A (and/or 3605B) working together to perform the fetch, decode, and execute cycles for every instruction in the instruction set for the noted segments of the program 3633.

The disclosed method of image processing may alternatively be implemented in dedicated hardware such as one or more integrated circuits performing the functions or sub functions of the various computational routines. Such dedicated hardware may include graphic processors, digital signal processors, or one or more microprocessors and associated memories.

In order to be able to compare and integrate the information carried by data sets of two images, at least one of the respective sets of imaging data has to be transformed so that both sets refer to a single coordinate system. In the field of optical imaging, this transformation is referred to as "registration" and the images "aligned" to refer to a single coordinate system are referred to as "registered" images.

B. Processing Registered 2D and 3D Images

The following disclosure relates to a method which extends the capabilities of 3D imaging, such as the conventional micro-CT, and allows calibrating a 3D image data by using complimentary and/or higher resolution data obtained by a range of 2D microscopic techniques. One application of the integration data obtained in such way is for the geological characterization of core materials/samples. Specifically, the disclosed method relates to registering image data of 2D images on and within 3D-images.

Pixel-to-voxel identification of 2D microscopic image data within a 3D image volume at similar resolutions allows the mapping of X-ray grey scale levels in the 3D image to a range of properties obtained from microscopy techniques and is used for studying properties including at least one of mineralogy, elemental composition, surface energy and acoustic/elastic properties. Whilst conventional X-ray micro-CT has a resolution of about 1 micron, microscopic techniques allow the probing of features and properties at scales down to nanometers. The ability to align and map 2D images into 3D images of at least partially overlapping spatial regions within a sample allows information on characteristics to be obtained that are currently considered too fine for X-ray CT analysis. The registered and processed images can be arbitrarily oriented, scaled and translated with respect to each other. Furthermore this advantageous capability of the disclosed method is also applicable in the case of registration of processing of two 3D images, where the two registered 3D images may also be arbitrarily oriented, scaled and translated with respect to each other. It should be noted that in the case of registration between 2D and 3D images, the partial overlap is a line or a surface of overlap between the 3D volume imaged by the 3D imaging technique, and the arbitrarily oriented plane, located on or within the sample, that is imaged by way of 2D imaging. In the case of 3D to 3D registration, the partial overlap is typically a spatial overlap between the two or more 3D regions of the sample that are imaged by one or more respective 3D imaging techniques.

The mapping performed by the disclosed method allows the correlation of conventional sedimentological data (e.g. data related to core descriptions, petrography, geofacies, geological rock type, mineral phases, mineral origins, elastic/acoustic properties, surface chemistry) derived from a range of 2D microscopy techniques, to 3D image data derived via micro-CT analysis (e.g. data related to attenuation, grain shapes, grain connectivity, pore connectivity, pore shapes). Microscopy techniques can probe down to nanometers, which is below micro-CT resolution. The obtained high resolution data can then be correlated directly to X-ray attenuation data from 3D micro-CT images. Thus, conventional sedimentological information can be correlated to data relevant to the prediction of petrophysical properties (e.g. permeability, drainage capillary pressure, acoustic and seismic properties, resistivity, NMR) and reservoir engineering properties (e.g. relative permeability, residual saturation, imbibition capillary pressure).

Integrated Information Obtained from Registering 2D Images to 3D Images

The details of the method are shown in FIG. 1. Once a sample of porous material is extracted, a 3D image is obtained in step 102, for example, by microtomography. One or more 2D sections or exposed planar surfaces from the sample, the sections being from a field of view of the tomographic equipment, are then collected and prepared for microscopy/spectroscopy in step 104. The remainder of core material can be used for quality control experiments (e.g., Helium and Mercury porosimetry).

The microscopy/spectroscopy is performed in step 106 by any one or more of the following techniques:
  Scanning electron microscopy (SEM); secondary & backscattered;
  Optical microscopy;
  Scanning acoustic microscopy;
  Laser confocal microscopy
  Focused Ion Beam scanning electron microscope (FIB-SEM);
  Energy Dispersive Spectroscopy (EDAX);
  Secondary Ion Mass Spectroscopy (SIMS);
  Spectroscopic techniques, including but not limited to Infrared, UV-visible and Raman spectroscopy; and
  Other microscopy or spectroscopy techniques The obtained microscopy/spectroscopy 2D image data is processed in a conventional technique to extract the properties (step 110) of various structures of the sample in 2D across a range of length scales (nanometer to micron scale). This range allows analysis to be made of properties such as mineralogy, surface properties, local surface interactions, acoustic properties, etc. As an example, standard petrographic analysis via optical microscopy allows the measurement of properties associated with at least one of the:
  Porosity;
  Mineralogies (e.g. quartz, feldspar, calcite, clays, pyrite, etc.);
  Identify grain boundaries, cementing phases;
  Identify geofacies types; and
  Geological rock type.

Step 108 of the method performs pixel-to-voxel registration of the one or more 2D images on the 3D image. Step 110 performs conventional 2D image analysis, e.g. spectrographic analysis. This allows quantitative integrated data to be obtained, in step 112 of the method, that can add value to data obtained solely by a single technique. One application of the integrated information is in performing direct quality control on 3D image data by comparison with a high resolution, high quality 2D microscopic analysis data. The integrated data can also be used to directly correlate pore and mineral phase information from high-resolution 2D microscopy images to data obtained from 3D images with sub-CT or conventional CT resolution. Such correlation can be used for any one of the following:

Direct testing of microporosity measurements;
  Populating microporosity data with grain/pore size information from sub-CT resolution scales;
  Populating 3D image data obtained from micro-CT with information obtained from the 2D microscopy and spectroscopic techniques (e.g., mineralogy, cementation, diagenetic history, higher resolution (micro) porosity, effective permeability, grain size, pore size at sub micron resolutions, acoustic properties and surface chemical characteristics).

Also, using the above described data correlation, a range of physical properties can be simulated in the optional step 114, including relative permeability of different fluid phases, resistivity, dielectric response, NMR response, and acoustic seismic response. Information on typical applicable simulation methods can be found in:

Digital core laboratory: *Petrophysical analysis from 3D imaging of reservoir core fragments*, C. H. Arns, F. Bauget, A. Ghous, A. Sakellariou, T. J. Senden, A. P. Sheppard, R. M. Sok, W. V. Pinczewski, J. Kelly, and M. A. Knackstedt, *Petrophysics*, 46(4), 260-277, 2005.
  C. H. Arns, A. P. Sheppard, R. M. Sok and M. A. Knackstedt, *NMR petrophysical predictions on digitized core images Petrophysics*, 48 (3), 202-221 (2007)
  *Archie's exponents in complex lithologies derived from 3D digital core analysis*, M. Knackstedt, C. Arns, A. Sheppard, T. Senden, R. M. Sok, W. Pinczewski and M. Ioannidis, Society of Petrophysicists and Well Log Analysts 48$^{th}$ Annual Logging Symposium, *Paper Z*, Jun. 4-6, 2007, Austin, USA.

Examples of Application of the Technique

Figures 2A, 2B:
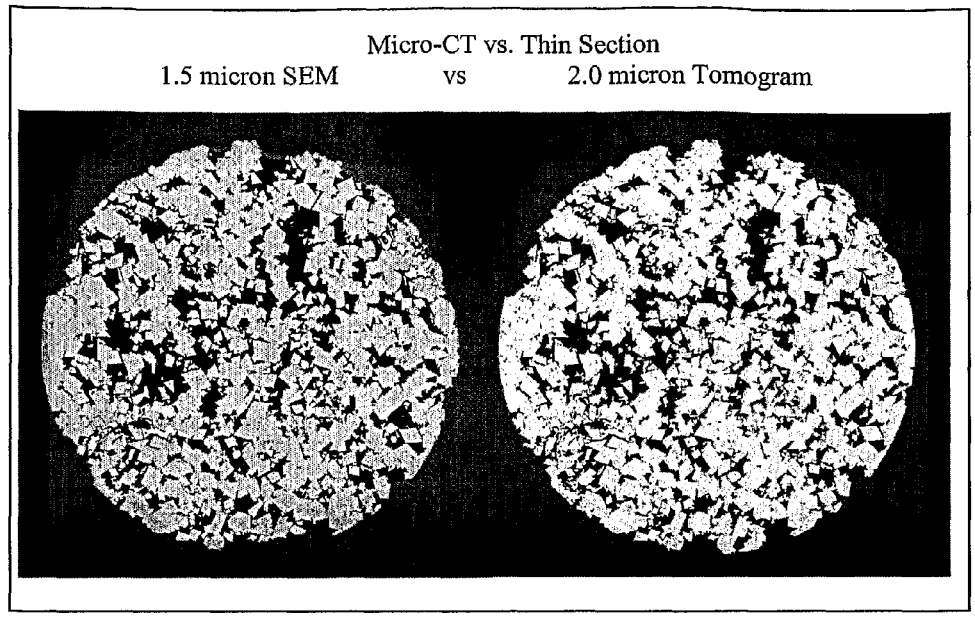
FIG. 2A and FIG. 2B show a 2D electron microscopy image and a 3D tomographic image, respectively.
Figure 3:
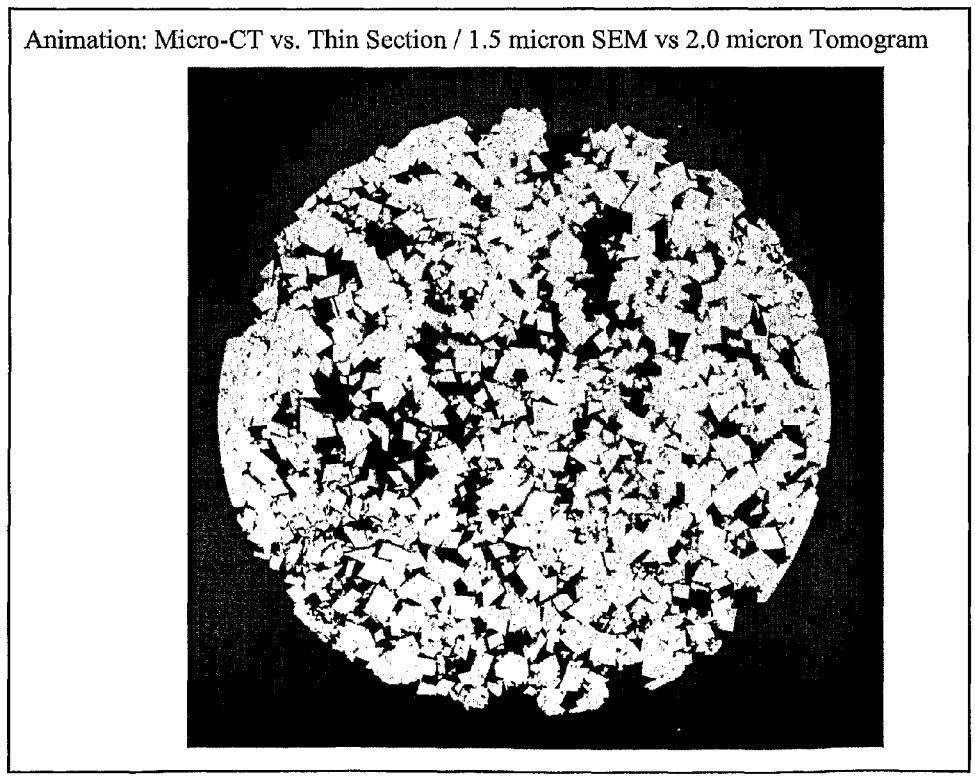
FIG. 3 shows the final frame from an animation of the registered images from FIGS. 2A and 2B.
Figure 7:
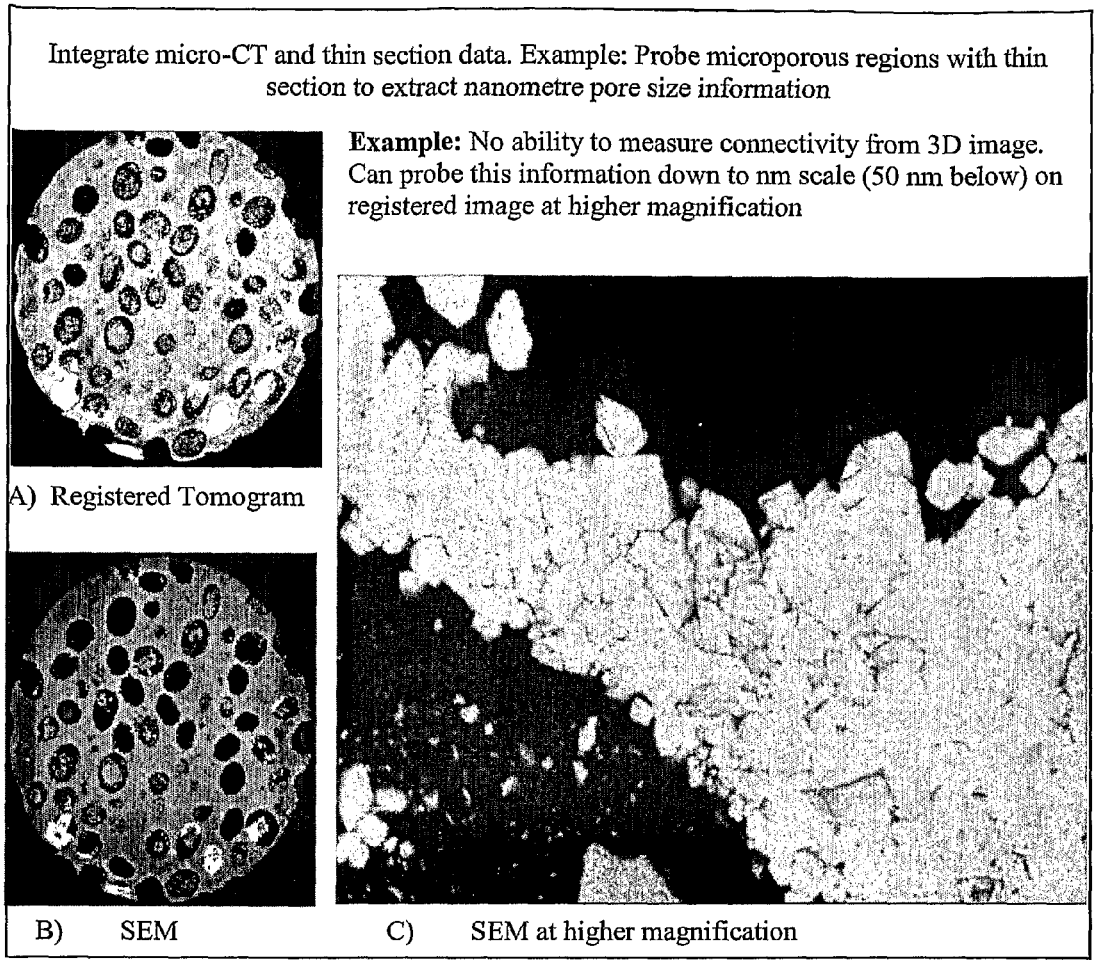
FIG. 7 shows an integrated image obtained by integrating pore structural information obtained from a 2D image into a 3D image data.

1. In one example, direct quality control on 3D image data can be achieved by comparing it with data from standard 2D microscopic analysis. FIGS. 2 and 3 illustrate pixel to voxel registration of a rock sample, most pores of which are resolvable on the micro-CT data. FIG. 2A shows an SEM image and FIG. 2B shows the respective tomographic slice registered via the disclosed method, as referred to in Step 108 (FIG. 1). There is a direct correspondence of the 2D image with the voxels of the 3D image. Any variations are primarily due to sample preparation for microscopy analysis.

2. In another application, direct correlation of attenuation information from 3D image data to enhanced information from 2D microscopic analysis can be performed. FIG. 4A shows an example of a 2D optical microscope image of a sandstone sample. Extensive variations in mineralogy are observed; the mineral phase distribution can be mapped and a range of classical petrographic analyses can be undertaken. FIG. 4B, on the other hand, shows the corresponding registered slice from the 3D tomogram. Based on the direct correlation of attenuation information in the 3D image to mineralogical information derived from the optical microscopy image, the mineralogical information obtained from the microscopic technique can be correlated to populate/propagate the information within the 3D micro-CT image data.

Another example is illustrated in FIG. 5 which shows an image of a microscopic sample obtained at 50 nanometer resolution. FIG. 6 shows the registered slice from the tomogram obtained at 2.5 micron resolution. The grey-scale attenuation information from the micro-CT data can be directly correlated to the 50 nm scale information (e.g. pore size, pore shape, grain size and shape at higher resolutions).

3. The method also provides the ability to use the high resolution of the microscopy technique to identify various features, which are then spatially associated with the corresponding 3D micro-CT image. Once these features are identified for the regions of overlap between the 2D and 3D image, by spatial association, they can be deduced for the remaining 3D space. This approach effectively uses microscopy data to build additional information into the 3D image data. The images in FIGS. 7A to 7C show how grain size and pore size information from a 2D SEM image at 50 nm scales (the image of FIG. 7C) enables the generation of pore structural information that is embedded (mapped) into the 3D tomographic image of FIG. 7A. Thus, an integrated image data set is generated that combines data from the micro-CT image of FIG. 7A with the thin section data of FIG. 7B and FIG. 7C. Such integrated data enables probing microporous regions within the thin section to extract nanometer pore size information. The ability to probe image information down to nm scale (50 nm or below) on registered image at higher magnification allows measuring connectivity characteristics in the 3D image at these scales.

In one application, direct correlations between pore size and grey scale attenuation allow the pore size information of voxels to be propagated in 3D data, originally assigned simply a porosity value. Mineralogy information, acoustic/elastic properties and surface chemical information may also be mapped via stochastic techniques to optimally populate the 3D micro-CT data.

De-Warping: Geometric Image Correction

Some microscopes introduce geometric distortion in an image that is going to be registered with another image. This could, for example, mean that distances measured in the image between two objects may not concur with true distances between the objects. This geometric distortion needs to be removed before accurate quantitative information can be inferred, or before two images can be correctly registered in order to properly integrate their information. This process of removing such distortions from the images is referred to as de-warping.

The de-warping process consists of two stages. Initially, a warp transformation is determined which is associated with the observed distortions. Then, the inverse of the warp transformation is applied to the image to produce a geometrically corrected image.

An example of estimating the warp transformation is to acquire images of sets of points for which the true location is known relative to each other. This information is then used to build a smooth map between points in an undistorted image and points in the distorted image. An arbitrary collection of points can be used for this purpose. However, the accuracy of the correction will depend on how well one is able to determine the warp transformation. This again depends on the complexity and the smoothness of the correction.

The following describes an example method of how the warp transformation can be determined for 2D images in an automatic manner. The same principles are applicable also in the 3D case.

Figure 8:
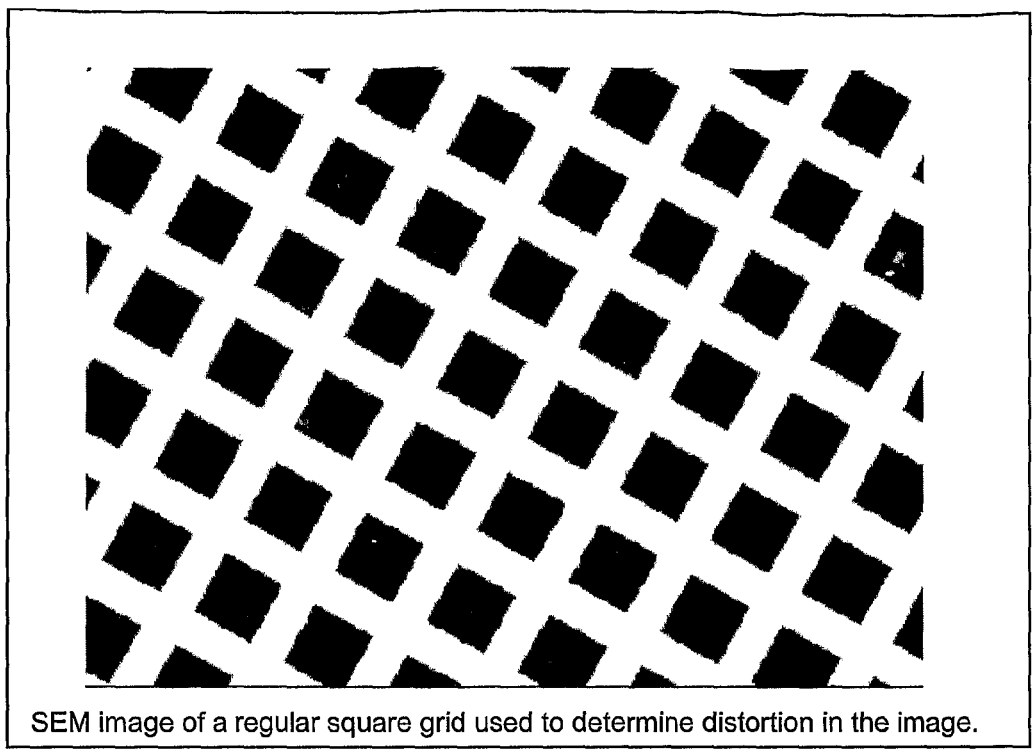
FIG. 8 shows a scanning electron microscope (SEM) image of a regular square grid used in a warp transformation.

Stage 1 of the de-warping process includes:

1. An image is taken of a regular square grid (FIG. 8). This image is referred to as the grid image and is used to determine distortion in the image.

Figure 9:
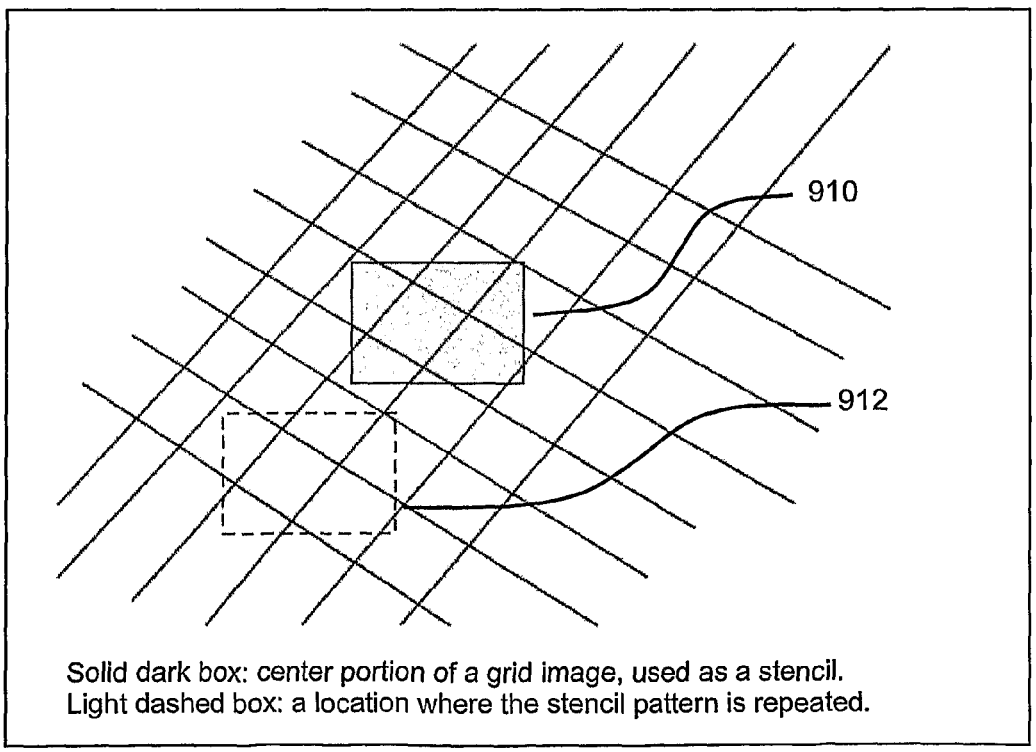
FIG. 9 shows a schematic diagram of a warp transformation stencil.

2. A small region 910 at the center of the grid image, large enough to contain a couple of grid cells in each direction and represented as a solid dark shaded box, is extracted. The region 910 is referred to as stencil (FIG. 9). The lightly shaded dashed box 912 indicates a location where the stencil pattern is repeated.

3. The cross correlation is computed between the grid image and the stencil, and correlation peaks are determined. The correlation peaks indicate where the same pattern re-occurs. For small distortions, simple translation is sufficiently accurate. For larger distortions rotations and scaling of the stencil may be required. In both cases, Fourier transforms are used to perform these computations in an efficient manner.

Figure 10:
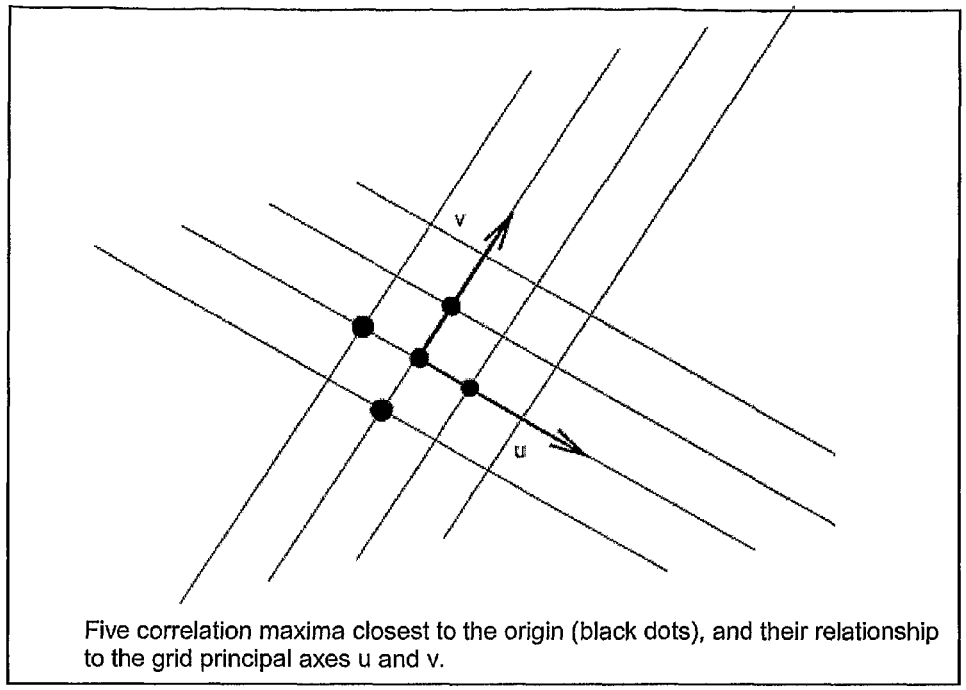
FIG. 10 shows five correlation maxima that are closest to the centre of the image in a warp transformation.

4. Five correlation peaks closest to the centre of the image and their relationship to the grid principal axes u and v, shown in FIG. 10, are determined. This, by construction, will be the center location itself, as well as the first correlation peak along each principal axis of the grid. These axes do not need to align with the axis of the image.

5. From these five correlation peaks, the principal axis of the grid can be determined. These axes are then used to estimate the correct location for the remaining correlation peaks, i.e., the location where they should have been in an un-distorted image.

6. Assigning correct locations to each correlation peak defines the warp transformation for this set of points. The warp transformation for locations between these points is then defined by an appropriate interpolation scheme.

Stage 2 de-warps of the image. At this point, the inverse of the warp transformation is applied to the distorted image in order to obtain an undistorted image: each pixel in the un-distorted image is mapped to its corresponding warped location, and the pixel value is found by interpolation in the distorted image. Working with a regular grid that is aligned with the undistorted image greatly simplifies the computation. For computational efficiency, this processing is performed as two steps:

1. Compute warp parameters (translation, rotation etc.) on a regular grid which is aligned with the un-distorted image.

Figures 11A, 11B:
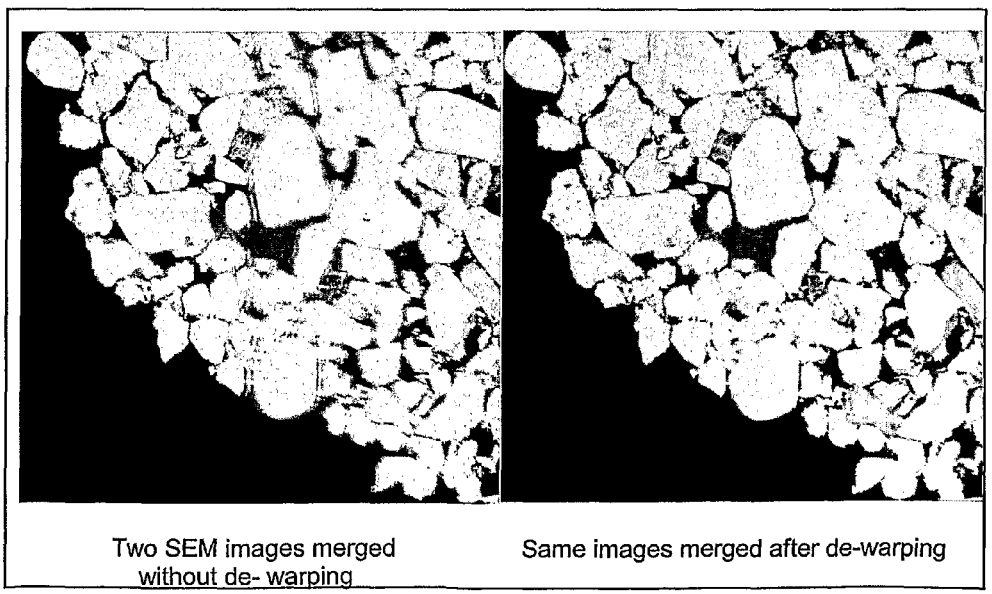
FIG. 11 shows an image obtained from images that, before being registered, have either been de-warped (FIG. 11B) or not been de-warped (FIG. 11A).

2. Find warp parameters for each image point by interpolation on the regular grid. The effect the process of de-warping can have on the quality of an integrated image is shown in FIG. 11. It is apparent from observation there that the quality of an integrated image obtained from de-warped SEM images (FIG. 11B) is greater to that obtained if the images are not de-warped (FIG. 11A).

It should be noted that the above described de-warping method is illustrative and other methods can also be used.

C. Processing Registered 3D to 3D Images

Other applications will now be described that rely on accurately registering arbitrarily oriented (e.g. rotated, scaled, shifted) 3D images to 3D images. The integrated information obtained as a result greatly extends the capabilities of conventional micro-CT imaging by allowing one to measure physical properties on the same porous material under a range of conditions after many complex experiments have been undertaken on the material.

If a series of 3D images obtained over a significant period of time can be registered in 3D, fluid phase distributions can be directly mapped in 3D at the pore scale after significant ageing or after long equilibration times. A full range of desired physical properties can then be simulated on the basis of the image data. These include relative permeability (permeability of multiple fluid phases within the porous material), resistivity of rock populated by multiple fluid phases, elastic response properties, NMR response and dynamic capillary pressure (see e.g., methods described in: "Digital core laboratory: Petrophysical analysis from 3D imaging of reservoir core fragments", C. H. Arns, F. Bauget, A. Ghous, A. Sakellariou, T. J. Senden, A. P. Sheppard, R. M. Sok, W. V. Pinczewski, J. Kelly, and M. A. Knackstedt, *Petrophysics*, 46(4), 260-277, 2005). The fluid distributions can be directly compared to pore network model results and be used as a calibration tool for the accuracy of pore scale modeling techniques.

The disclosed method relates generally to visualizing and quantifying the change in pore structure, mineral phase structure and the distribution of multiple fluid phases within the pore space of a three dimensional porous media. From the direct quantification of the changes in porous media, a range of physical properties of porous materials under varying saturation states and varying surface chemical conditions can be estimated. These properties include relative permeability of different fluid phases, resistivity, dielectric response, NMR response, and elasticity. Materials include reservoir core material, soils, granular materials and other composites.

The disclosed method addresses an essential requirement for understanding multiphase flow, rock mechanics and petrophysical properties under realistic conditions. For example, it is known that fluid imbibition characteristics change after ageing of a core in crude oil (see e.g., Morrow, "*Wettability and its effect on oil recovery*", SPE 21621, published in Journal of Petroleum Technology, December 1990, p. 1476: and Graue et al., "*Alteration of wettability and wettability heterogeneity*" Journal of Petroleum Science & Engineering, Vol. 33, pp. 3-17). Other measurements also require the ability to conduct experiments at reservoir temperatures and overburden pressure. It is not always practical to undertake such experiments without sample movement occurring or removing the sample from the micro-CT apparatus. The proposed method allows one to image a sample, undertake a range of complex experiments on the sample in a laboratory and then re-image the sample and register the 3D image taken before and after the experiments, by way of software implemented by the described algorithms.

Method for Integrating Data Associated with 3D to 3D Registered Images

The steps of this method are shown in FIG. 12. The method begins with step 1202 of taking a 3D image of the porous material of interest. This imaging defines an initial reference state A. Typically, the studied sample in this state is either dry (FIG. 13) or fluid saturated (FIG. 14). The image data is then stored in memory in step 1204.

The next step 1206 involves performing one or more experiments on porous material which can lead to a possible structural or chemical change in the pore structure, mineral phase structure or pore fluid distribution. Examples of experiments could include any one of:

Fluid Displacement studies on porous material, that could be in the form of;
  Immiscible fluid displacements;
  Drilling fluid invasion;
  Flooding with surfactants, microorganisms, polymers, gels or colloids; or
  Miscible fluid displacement
Reactive effects, that could include any one of the following;
  reactive flows;
  flooding with solvent;
  deposition and reactive fouling;
  biofouling.
Mechanical effects such as:
Grain mineralogy/fracturing;
Clay swelling, attachment and detachment; or
Acoustic stimulation of fluids
Fluid effects on pore and mineral phase structure;
Fluid exchange;
Pore plugging via particulates, polymers and/or aqueous solutions;
Clay migration (native);
Colloid attachment/detachment and fouling;
Clay swelling;
Wettability distributions including;
  Correlate fluid distributions to pore size and structure;
  Effects of ageing in crude on wettability and pore fluid distributions
  Measurement of surface chemical properties of liquid/liquid and liquid/solid interfaces (e.g., contact angle, presence of fluid films;

The method further includes, after conducting one or more experiments, re-imaging the sample material, in step 1208, and storing the re-imaged data, in step 1204. The sample may be re-imaged multiple times. Instead of performing experiments with the sample, step 1206 may be associated with obtaining sample subsections for a higher resolution imaging. As a result, a pair of images is generated, which represent either images taken before and after an experiment, or images obtained with different imaging resolution. The two sets of data can then be used, in steps 1210 and 1212, by aligning and superimposing the 3D data from two of the obtained images by performing voxel registration of the 3D images to obtain integrated imaging information. Such an alignment and integration can then be performed between another pair of images. The process of integrating the information of two or more images may include determining a physical or chemical property of a particular area of the sample, based on information from both images. It may also involve quantifying changes in pore structure, mineral phase structure or pore fluid distribution.

Returning now to FIGS. 13 and 14, the figures show an air/water phase in porous rock after fluid uptake. The performed 3D registration allows the pore scale distribution of fluids to be directly visualized and quantified in 3D. In particular, FIG. 14 shows the fluid distribution in the rock from FIG. 13, after performing an experiment on uptake of a wetting fluid into the dry rock.

FIG. 15 shows a snapshot from a 3D video illustrating the fluid distribution derived from image registration of the pair of 3D image data files.

The re-imaging of the sample material can be repeated many times—after each conducted experiment, or after a series of experiments. The image data is again stored in the memory of the computer or another electronic system that deals with the data processing (usually a hard drive). Thus, there is no time limitation to the length of time between the acquisitions of different images. Voxel-to-voxel registration of two or more of the stored images then allows for the information from any number of images to be combined, thus adding to the value of all experiments.

The proposed method for the generation of integrated images from an arbitrary number of experiments conducted over an arbitrary time period is distinct from the two experimental methods that comprise the current state of the art. In the first method, represented by M. Prodanović et al "3D image-based characterization of fluid displacement in a Berea core" Advances in Water Resources 30, 2007, p 214, all experiments are conducted in the beamline, meaning that the nature and duration of experiments are limited by beamline availability, space considerations and the need for temperature and mechanical stability. In the second method (see e.g. Dautriet et al "Laboratory determination of stress path dependency of directional permeability of Estaillades limestone", Symposium of the Society of Core Analysts, Abu Dhabi, November 2008, paper SCA2008-26), the sample is imaged, then taken away for experimental modification, then returned to the beamline for re-imaging, but no effort is made to register the different images. In this case, no directly integrated image information is obtained and the only results are spatial averages.

The final step 1212 involves, using the integrated information obtained from the registered 3D images in step 1210, to quantify the change in pore structure, mineral phase structure or pore fluid distribution. The implications of these changes to physical properties of the porous material can also be investigated. For example, from the direct quantification of the pore scale distribution of wettability distributions and directly simulate a range of physical properties of these porous materials under varying saturation states and varying surface chemical conditions can be examined. The properties of interest typically include relative permeability of different fluid phases, resistivity, dielectric response, NMR response, and elasticity.

Figures 16A, 16B:
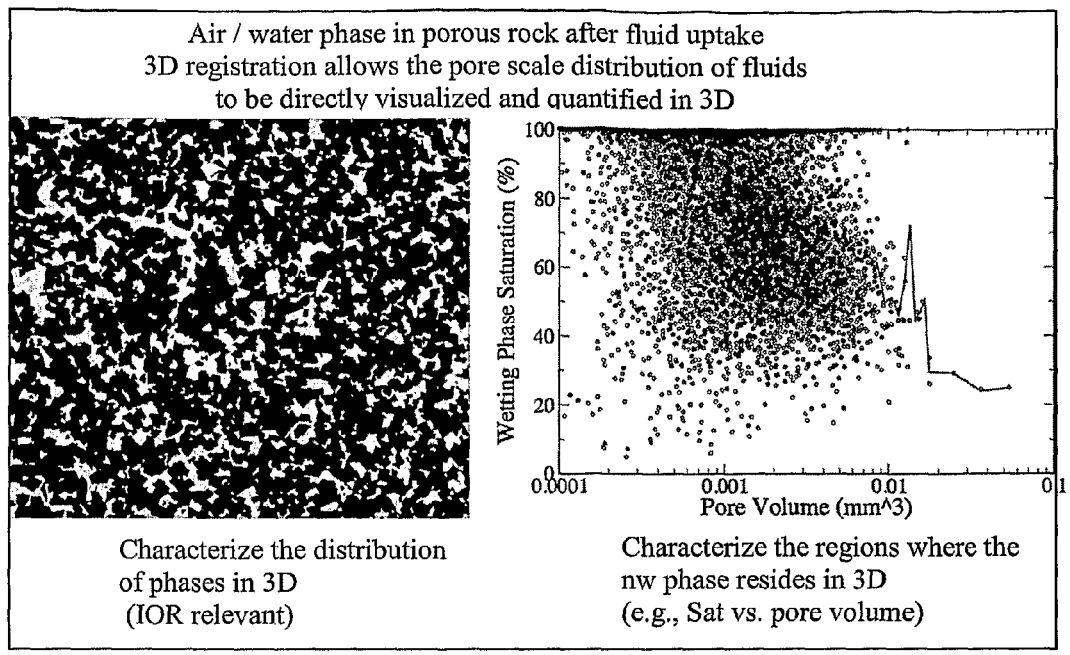

FIGS. 16A and 16B illustrate the correlation between the distribution of pore sizes and air/water fluid content. 3D registration allows the pore scale distribution of fluids to be directly visualized and quantified in 3D (FIG. 16A). FIG. 16B shows a distribution of the regions where the non wetting (air) phase resides in 3D. In this case the system was originally water wet so the residual air phase resides primarily in the larger pores and the water phase is concentrated in the smaller pores.

D. Example Applications

A number of examples of relevant experiments on porous material across a range of disciplines are now discussed, where the ability to quantify a possible structural or chemical change in the pore structure, mineral phase structure or pore fluid distribution is important.

1. Fluid Displacement description on porous materials at the pore scale. First some applications of imaging porous materials are described under different wettability conditions and saturation states and re-imaged. Several phases can be imaged within the porous material. Fluid displacement property related experiments can include;
   a. Immiscible fluid displacements in Core Analysis (Upstream Oil & Gas/Groundwater and Hydrology);
   Drainage and imbibition flooding at multiple saturation states.
   Drainage and imbibition under varying wettability states (oil wet, water wet, mixed wet large, mixed wet small).
   Probe the effect of ageing of crude oils on the distribution of hydrocarbons, brines, gases, etc. during and after flooding.
   Probe the distribution of ranges of fluids:
   Oil/Hydrocarbons
   Water/brines
   $CO_2$
   Muds
   Drilling fluids
   polymers
   Colloids
   Dispersants
   Pore plugging fluids (e.g, polymers, gels, microbial species)
   Testing of designer floods;
   Optimal brines for maximal extraction in pore structure
   Testing of pore scale distribution with varying oil phase/brine mixtures.
   Test efficacy of Improved/Enhanced Oil recovery strategies (e.g., WAG injection and Colloid stimulation)
   Imaging of mud invasion into core material (formation damage).
   b. Miscible Fluid Displacements:
   Miscible flooding (EOR)
   Groundwater remediation;
   Quantify distribution of toxic or radioactive spill at pore scale
   Test methods for containment (chemical, hydrological)

2. Fluid effects on pore and mineral phase structure: Effect of fluid exchange on the pore structure, mineral structure and wettability of porous materials. (e.g., effect of dilution of brine on pore topology);
   a) Clay migration (native);
   b) Colloid attachment/detachment and fouling; and
   c) Clay swelling.

3. Wettability distributions. Characterize the wettability state of fluid/fluid and fluid/solid interfaces in porous materials occupied by multiple fluid phases. These include;
   a. Correlating fluid distributions to pore size and structure
   b. Measurement of surface chemical properties of liquid/liquid and liquid/solid interfaces (e.g., contact angle, presence of fluid films)

4. Reactive effects. Undertake a direct pore scale investigation of the effect of reactive species on the pore and mineral phase structure of porous materials. Fluid wettability studies can also be undertaken at multiple time steps.
   a. Reactive flows;
      Supercritical $CO_2$
      Acidic flooding
      Solvent based flooding
   b. deposition and reactive fouling;
   c. biofouling.

5. Mechanical effects: Effect of mechanical stress and strains on the pore and mineral phase structure of porous materials. These can include;
   Grain mineralogy/fracturing
   Clay swelling, attachment and detachment
   Acoustic stimulation of fluids. Test use of acoustic waves to enhance hydrocarbon recovery.

E. Image Registration Workflow

It has to be noted that the hereinafter described registration workflow is applicable to both 2D to 3D and 3D to 3D image registration. The same registration workflow, with minor changes to the definitions, is also applicable to 2D to 2D image registration.

Definitions

Let T represent an entire discrete-image and let $T_{i,j,k}$ represent the intensity of the discrete-image at index (i,j,k). Let F be another discrete-image and, similarly, let $F_{i,j,k}$ represent the intensity of the discrete-image F at index (i,j,k). Furthermore let $I^{(n)}$ be the discrete-image created from discrete-image I by down-sampling by a factor of $d_n$. Always define $d_0=1$, so that $T^{(0)} \Leftrightarrow T$ and $F^{(0)} \Leftrightarrow F$. The discrete-image T is the moving-discrete-image and F is the fixed-discrete-image. It is T which is moved (or transformed) so that becomes registered with the fixed-discrete-image. For example, T could be a 2D SEM image which is to be registered with F—the 3D micro-CT image. If T is a 2D image, it is simply interpreted to be a plane in three-dimensional space, that is, the third indexing dimension is fixed, k=0 say. Or, as another example, T could be a 3D wet-micro-CT image which is to be registered with F—the 3D dry-micro-CT image. The discrete images F and T could also be a pair of 2D images (for example, the partial segments 174 of an SEM thin-section image as illustrated in the diagram of FIG. 17) and with minor notational changes the below method applies for 2D to 2D registration.

Let $t^{(n)}:\Omega_t \to \mathbb{R}$ be the interpolated-image version of the discrete-image $T^{(n)}$, with $\Omega_t \subset \mathbb{R}^3$, Similarly, let $f^{(n)}:\Omega_f \to \mathbb{R}$ be the interpolated version of the discrete image $F^{(n)}$, with $\Omega_f \subset \mathbb{R}^3$, Define $\Psi^{(n)}: \mathbb{R}^{m^{(n)}} \times \mathbb{R}^3 \to \mathbb{R}^3$, to be a spatial-transformation, which, given a set of transform parameters $\phi \in \mathbb{R}^{m^{(n)}}$, maps 3D points into 3D points.

Let $\mathcal{M}^{(n)}: \mathbb{R}^{m^{(n)}} \to \mathbb{R}$ define a distance-metric which indicates the quality of the registration between the two interpolated-images $t^{(n)}$ and $f^{(n)}$. We also require that the lower the value of $\mathcal{M}^{(n)}$ the better the registration, the higher the value of $\mathcal{M}^{(n)}$ the poorer the registration.

Given initial discrete-images $t^{(0)}$ and $f^{(0)}$, transform-parameters $\phi^*$ needed to be found which will bring the two images into registration. This can be restated as the optimization problem:

Registration Optimization Problem:

Given the spatial transformation $\Psi^{(0)}$, the distance-metric $\mathcal{M}^{(0)}$ and the images $t^{(0)}$ and $f^{(0)}$, find $\phi^* \in \mathbb{R}^{m^{(0)}}$ such that:

$$\phi^* = \min_{\phi \in \mathbb{R}^{m^{(0)}}} (\mathcal{M}^{(0)}(\phi))$$

In general, $\mathcal{M}^{(0)}$ is a complicated function with many local-minima and is computationally expensive to evaluate (especially for the full resolution images). Hence, local numerical optimization methods (simplex method, Powell's direction set method, gradient descent, etc) alone are unsuccessful at finding (an approximation to) $\phi^*$. The following section presents a multi-resolution multi-start global optimization method capable of solving the Registration Optimization Problem.

General Method

1. Choose: down-sampling factors $d_0, \ldots, d_N$, spatial-transformations $\Psi^{(0)}, \ldots, \Psi^{(N)}$, distance metrics $\mathcal{M}^{(0)} \ldots \mathcal{M}^{(N)}$, and number of best transform-parameters $J^{(0)}, \ldots, J^{(N)}$. See below for example selections of these variables.

2. Define $\Phi^{(N)} \subset \mathbb{R}^{m^{(N)}}$ to be some finite sampling of points from $\mathbb{R}^{m^{(N)}}$ and let $P^{(N)}$ be the number of elements in the set $\Phi^{(N)}$. For each $\phi_p^{(N)} \in \Phi^{(N)}$, $p=1, \ldots, P^{(N)}$, evaluate $m_p^{(N)} = \mathcal{M}^{(N)}(\phi_p^{(N)})$. See below for an example $\Phi^{(N)}$.

3. Create the set $\hat{\Phi}^{(N)} = \{\hat{\phi}_j: \hat{\phi}_j = \phi_{pj}^{(N)}, j=1, \ldots, J^{(N)}\}$, where $p_j$ is defined such that $m_{pj}^{(N)}$ is the j-th smallest value of all $m_p^{(N)}$, $p=1, \ldots, P^{(N)}$.

4. Set n=N.

5. Set n=n−1. If n≥0, continue to 6, else go to 9.

6. For each j=1, \ldots, $J^{(n+1)}$ use a local numerical optimization algorithm (e.g. Powell's direction set minimization method) with starting point $\hat{\phi}_j^{(n+1)} \in \hat{\Phi}^{(n+1)}$ to calculate a local-minimum of $\mathcal{M}^{(n)}$ Denote the transform-parameters for which the local-minima were calculated as $\hat{\phi}_j^{(n)}$, and the distance-metric value at those local-minima as $\hat{m}_j^{(n)} = \mathcal{M}^{(n)}(\hat{\phi}_j^{(n)})$.

7. Create the set of transform-parameters; $\hat{\Phi}^{(n)} = \{\hat{\phi}_j: \hat{\phi}_j = \hat{\phi}_{pj}^{(n)}, j=1, \ldots, J^{(n)}\}$, where pj is defined such that $\hat{m}_{pj}^{(n)}$ is the j-th smallest value of all $\hat{m}_p^{(n)}$, $p=1, \ldots, J^{(n)}$.

8. Go to 5.

9. Set $$\hat{\phi} = \min_{\varphi \in \hat{\Phi}^{(0)}} (\mathcal{M}^{(0)}(\varphi))$$

to be the optimal set of parameters which register the $t^{(0)}$ image with the $f^{(0)}$ image.

10. Create a new pair of discrete images in the registered state, using the optimal $\hat{\phi}$ transform-parameters;

Step 1 defines specifics about down-sample factors, the allowable spatial-transformations and the types of distance-metric used to evaluate the quality of the registration achieved given a set of transform-parameters. Typically, the down-sample factors are chosen to be powers of 2, with $d_0=1$ and $d_{n_o} \leq d_{n_2}$ for $n_0 < n_1$. An example sequence might be $d_0=1$, $d_1=2$, $d_2=4$, $d_3=8$, $d_4=16$ and $d_5=16$. The maximum down-sample factor should be chosen so that characteristic features are preserved in the lowest resolution image.

The spatial-transforms $\Psi^{(0)}, \Psi^{(1)}, \ldots, \Psi^{(N)}$ define how coordinates from the $t^{(n)}$ domain $\Omega_t$ are registered/overlayed into the $f^{(n)}$ domain $\Omega_f$. One possibility is to choose all the spatial transforms be identical, $\Psi^{(0)} \Leftrightarrow \Psi^{(1)} \Leftrightarrow \ldots \Leftrightarrow \Psi^{(N)} \Leftrightarrow \vec{\Psi}$. This was the case for registering the examples in the Figures and $\vec{\Psi}$ was chosen to be the 3D similarity transform ($\vec{\Psi}: \mathbb{R}^7 \to \mathbb{R}$ 7 degrees of freedom comprising 3 translation, 3 rotation and an isotropic scaling parameter).

There are a variety of practical distance-metrics which may be chosen and, again, a reasonable choice is to have the same mathematical form for distance-metric for each search level n, $\vec{\mathcal{M}}^{(n)}$ say, with the only variation between the search levels being that the distance-metric is evaluated using the corresponding down-sampled image pair. Useful cost-metrics include: the correlation-coefficient, correlation-ratio and (normalised) mutual-information. For the registered examples in the Figures, $\vec{\mathcal{M}}^{(n)}$ were chosen as the negative of the correlation coefficient:

$$\vec{\mathcal{M}}^{(n)}(\phi) = -\frac{\sum_{l=1}^{L}(t^{(n)}(x_l) - \overline{t^{(n)}})(f^{(n)}(\vec{\Psi}(\phi, x_l)) - \overline{f^{(n)}})}{(L-1)\sigma_{t(n)}\sigma_{f(n)}},$$

where $\overline{t^{(n)}}$ is the mean and $\sigma_t(n)$ the standard deviation of the $t^{(n)}$ image intensities at sample coordinates $x_l$, $f^{(n)}$ is the mean and $\sigma_f(n)$ standard deviation of the $f^{(n)}$ image intensities at sample coordinates $\vec{\Psi}(\phi, x_l)$, and the sample spatial coordinates are taken from the intersection of the image domains $x_l \in (\Omega_t \cap (\vec{\Psi}^{-1}(\phi) \cdot \Omega_f))$. Here $\vec{\Psi}^{-1}$ is the inverse of $\vec{\Psi}$ such that $\vec{\Psi}(\vec{\Psi}^{-1}(x)) = x, \forall x \in \mathbb{R}^3$.

The values for $J^{(n)}$ are the number of best-ranked transform-parameters which are passed from search-level n to search-level n−1. Typically $J^{(0)}=1$ and $J^{(n_0)} \leq J^{(n_2)}$ when $n_0 < n_1$. An example sequence for $J^{(n)}$ is: $J^{(0)}=1$, $J^{(1)}=1$, $J^{(2)}=1$, $J^{(3)}=4$, $J^{(4)}=32$, $J^{(5)}=64$.

In Step 2, the goal is to find at least one set of transform-parameters which is "close" to the desired set of transform-parameters $\phi^*$. In this step, an exhaustive type search can be conducted to discover sets of transform-parameters which are likely to yield the desired registration at higher resolutions. Typically, the set $\Phi^{(N)}$ is defined as a regular grid of transform-parameters, $\Phi^{(N)}=\{\phi_\alpha:\alpha\in\mathbb{Z}^{m^{(N)}}, \alpha=0,\ldots,A\}$, where $\alpha=[\alpha_0, \alpha_1, \ldots, \alpha_m(N)]^T$ is a multi-index and $$\varphi_\alpha = \begin{bmatrix} \varphi_0^{min} + \alpha_0\delta_0 \\ \varphi_1^{min} + \alpha_1\delta_1 \\ \vdots \\ \varphi_{m(N)}^{min} + \alpha_{m(N)}\delta_{m(N)} \end{bmatrix},$$

with $\phi^{min}\in\mathbb{R}^{m^{(N)}}$ being a lower limit for the transform-parameter components, and $\delta\in\mathbb{R}^{m^{(N)}}$ the step-size of the grid in the transform-parameter space. A minimal translation range can be chosen so as to ensure that $\Omega_f\cap(\Psi^{(N)}(\phi)\cdot\Omega_t$ is non-empty for all $\phi\in\Phi^{(N)}$, with typical translational step-size chosen to be the down-sampled voxel size. Rotational values range from −180° to 180° with step-size of ≈3$^\alpha$. Step 2 is essentially a global optimisation method applied to the low resolution images in order to find a set of transformation parameters which are within the "capture radius" of the global minimum of the distance-metric. This paragraph describes an "exhaustive search" global optimisation method, however, other global methods may be applied in Step 2 in order to discover transformation parameters (or multiple sets of parameters) which are "close" to the optimal registration parameters.

Step 3 orders the sets of transformation parameters from best to worst registration. In iterative fashion, Step 4 to Step 8 perform incremental improvements to the sets of transformation parameters found in Step 2 by performing local-optimizations on successively higher resolution images.

Step 9 selects the transformation parameters which yield the optimal registration and Step 10 performs a re-sampling of the images (using these optimal transformation parameters) to generate a pair of registered discrete-images which can be directly compared for subsequent analysis.

Algorithm

An algorithm for the implementation of the above discussed registration method is shown in FIG. 17, for effecting registration between a 3D image 1702 and a 2D image 1708. The initially obtained image 1702 is pre-processed by processor 3605A, by way of filtering, masking etc., to obtain an image 1704 that is ready for registration. Similarly, individual images 1706 are also pre-processed to obtain the 2D operational image 1710. In particular, the pre-processing of the 2D sub-sections 1706 may comprise dewarping and stitching together subimages to obtain the single image 1710.

In step 1 of the algorithm of FIG. 17, a similarity transformation is selected by processors 3605A and 3605B for aligning the 2D image 1710 with the 3D image 1704. Seven degrees of freedom are involved in this transformation; 3 translation parameters, 3 rotation parameters and one scaling parameter. Negative values of the correlation-coefficients are used to evaluate the quality of the alignment, wherein a value of −1 indicates a perfect correlation.

In step 2, a low resolution pair images are used by processors 3605A and 3605B to obtain a set of initial estimates of the alignment between the images 1704 and 1710. The implementation of step 2 may take advantage of task parallelism to reduce the runtime of the step. More details on the implementation of task parallelism in this application will be provided further in the text. In step 3, a group of best transform parameters is selected to be used as starting-seeds for local optimization. At this point of the processing there is an approximate alignment between the images 1704 and 1710 at their lowest resolution.

In step 4, a loop counter is initialized by processors 3605A and 3605B with respect to the number of searches. In the following step 5, the loop counter is immediately decremented by 1 by processors 3605A and 3605B. If now the loop counter holds a value greater than, or equal to 0, the method proceeds to step 6. In step 6, the processors 3605A and 3605B refine the alignments from the previous search level n+1, by using local numerical optimization on the current higher resolution images. The step 6 implementation can take advantage of task parallelism for lower resolution images in which case 3605A and 3605B will each process a different subset of the start-seeds. For the higher resolution image pairs, where the RAM required for the images exceeds the physical RAM of a single computer processor, a data parallel strategy may be implemented, in which case 3605A and 3605B each calculate a separate portion of the metric relating to the relevant sub-image stored in the memory accessible from each processor. More details on such implementation will be provided further in the text. In step 7, the processor 3605A selects a group of best transform parameters from the current search level to be used as seeds for the next search level. In step 8, the loop is continued by returning to step 5.

An alternative route is taken if n is negative. In this case, after step 5 the processor 3605A and 3605B proceed to step 9, where the processors select the best transform parameters from search level n=0. These are the parameters which provide the lowest metric value in the full resolution searches. Using these parameters, in step 10, the processors 3605A and 3605B re-sample the 3D tomogram image to generate the slice corresponding to the 2D image. This results in the generation of two aligned 2D images 1714 and 1716, which are of the same size. These images can then be directly used for subsequent qualitative and/or quantitative analysis.

Steps 1 to 10 in FIG. 17 substantially define the registration method referred to in step 108 of the high level representation of the disclosed image processing method shown in FIG. 1. Similarly, FIG. 18 shows the registration step 1210 of the high level diagram of the disclosed method for image processing shown in FIG. 12.

The registration process shown on FIG. 18 is applicable to two 3D images 1802 and 1808. The image 1802 may be a 3D Micro-CT image of a dry core sample. In contrast, the image 1808 may be a 3D Micro-CT image of the same sample, after undergoing a particular experiment, where the experiment may include, for example introducing the core into a particular fluid, such as water, petrol or gas. Both images 1802 and 1808 are pre-processed by way of filtering and masking, using for example simple thresholding. As a result of the pre-processing, images 1804 and 1810 are obtained, respectively. Again, in step 1 processor 3605A uses a similarity transformation in order to align the two tomogram images 1804 and 1810. Again seven degrees of freedom are selected by processors 3605A and 3605B, comprising 3 translation parameters, 3 rotation parameters and 1 scaling parameter. A negative overlap percent metric is used, which simply counts the percentage of coordinates which have the same non-masked intensity in both images. A value of −100% indicates a perfect overlap of non-masked regions in the images.

Steps 2 to 9 are generally identical to these in FIG. 17. Step 10 is again the final step and includes processors 3605A and 3605B resampling the wet 3D tomogram image 1810 in order to generate a region corresponding to the dry 3D tomogram image 1804. As a result, a pair of 3D images 1814 and 1816 is obtained by processors 3605A and 3605B, which are of the same size and which can be integrated for quantative analysis purposes.

FIG. 19 shows in more detail various substeps of step 2 in FIGS. 17 and 18. Step 2 starts with step 2a, comprising processors 3605A and 3605B forming a regular grid in the 7-dimensional transform parameter space. Typically, the translation parameter step-size is the voxel side-length of the lowest resolution image. The z-axis rotational parameter step size is two degrees. The x-axis and y-axis rotational parameters, as well as the scaling parameter, can remain fixed (at values 0 degrees, 0 degrees and 1, respectively). Once the regular grid is formed, from step 2a the processor 3605A proceeds to step 2b of initializing the parameter k, by letting k be the number of points in the 7D parameter grid. In the following step 2c, the parameter k is reduced by 1 and the new parameter value is compared to 0 by processors 3605A and 3605B.

If the reduced k is greater than or equal to 0, processors 3605A and 3605B proceed from step 2c to step 2d, in which the respective processors 3605A and 3605B evaluate the metric for the transform parameters of the 7D grid point number k. If the metric value is lower than any of the best metric values obtained so far, the processors 3605A and 3605B replace the transform parameters which give the worst metric value with transform parameters number k. The conclusion of step 2d is for processors 3605A and 3605B to return to step 2c. Alternatively, if the value of the parameter k, as reduced in step 2c is negative, then from step 2c the processors 3605A and 3605B proceed to step 2e, which concludes the entire step 2. The negative value of the parameter k indicates that the exhaustive search of the 7D grid has been completed and that at least one set of transformation parameters have been identified which are within the capture radius of the metric global minimum. Here task parallelism may be implemented by dividing the K grid points amongst the different processors, such as 3605A, 3650B etc.). Each processor evaluates the metric for its subset of grid points. The groups of best parameters are collected from each processor and collated to form the final group of best transform parameters.

Parallel Implementation

In order for the above global-minimization method to be computationally feasible, there are two parallelization strategies which are used when implementing the above steps in software on high-performance Non-Uniform Memory Access (NUMA) architectures. The first is a task-parallelism strategy where individual tasks are performed independently on computational-units. The second strategy is a data-parallelism approach where each computational-unit contains only a subset of the discrete-image pair data.

Task-parallelism is of great advantage when calculating the distance-metric values $m_k^{(N)}$ in Step 2 of the above described workflow. At low resolutions each computational-unit can evaluate a subset of the $m_k^{(N)}$ values independently of other computational-units. When all computational-units have evaluated their subset of $m_k^{(N)}$ values, there is a result collection stage where the subsets of $m_k^{(N)}$ values are gathered from each of the computational units in order to rank the best transform-parameters as is carried out in Step 3. Likewise, task-parallelism can be used to advantage in Step 6, where each computational-unit can perform a subset of the iterative-optimizations, independently of other computational-units, in order to calculate the local-minima $\hat{\phi}_j^{(m)}$. Again, a result collection stage is used to gather the subsets of $\hat{\phi}_j^{(m)}$ values from each of the computational-units in order to rank them as is carried out in Step 7. Task-parallelism is of most advantage for the lower-resolution images ($t^{(N)}$, $t^{(N-1)}$, $f^{(N)}$ and $f^{(N-1)}$, for example) because the entire data of the underlying discrete-image pairs can be stored in the local-RAM of a computational-unit.

For the higher-resolution images ($t^{(0)}$, $t^{(1)}$, $f^{(0)}$ and $f^{(1)}$, for example), the data-parallel strategy is preferred. In this strategy, each computational unit only contains a subset of the discrete-image data. Step 7 is then performed using Master-Worker division of labour. The master computational-unit controls the iterative optimization algorithm. The iterative optimization requires multiple evaluations of the distance-metric in order to determine a local minimum. It is the evaluation of distance-metric which is performed in a distributed and parallel fashion. Each worker computational-unit is able to calculate a portion of the total distance-metric result based on the subset of image data held in its local-RAM.

E. Further Application Examples

X-ray micro computed tomography (CT) has an ability to generate detailed 3D images of pore structures on the micron scale. The X-ray tomogram provides phase information via the detected X-ray attenuation. This data is not as detailed and useful as that provided by various 2D microscopy techniques. For example, optical microscopy and scanning electron microscopy can provide information of the detailed mineralogical content of a sample. Scanning acoustic microscopy allows one to map the mineral acoustic (elastic) properties. Other microscopic techniques that can be performed on a 2D surface or thin section can give further information (e.g. mineralogy, surface properties, local surface interactions etc.) that is important to the understanding of the material properties of the studied core material (sample). One disadvantage is that the obtained data is in 2D. It would be greatly beneficial to obtain the enhanced information, available via 2D methods, in 3D. The method described here allows one to quantitatively propagate the information obtained from a 2D image onto a 3D tomographic data set.

Figure 20:
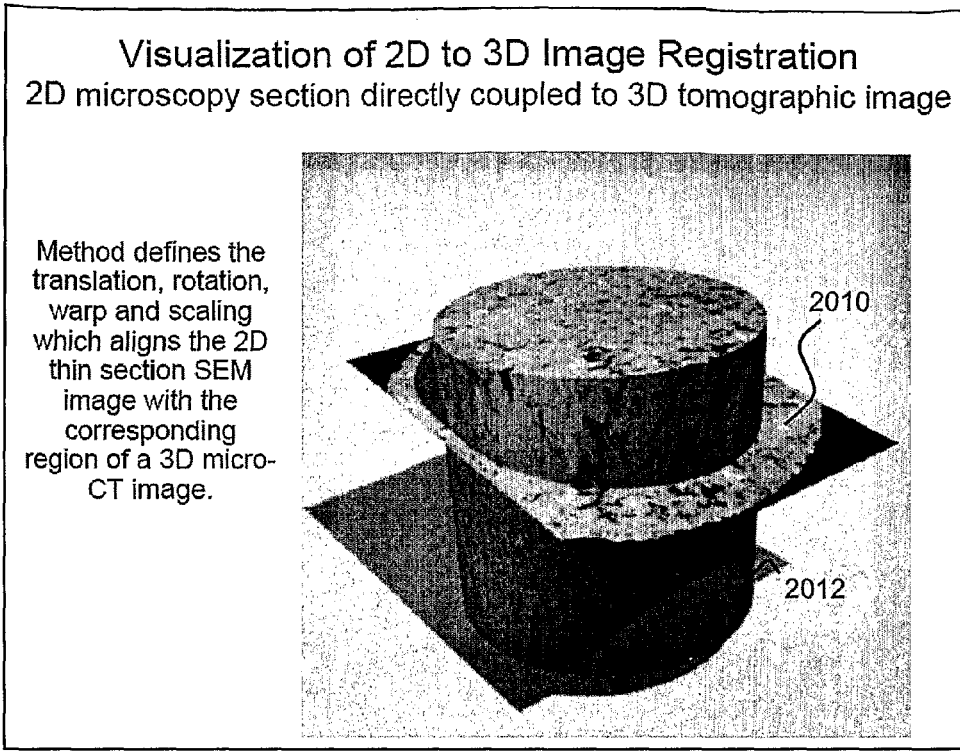
FIG. 20 shows a 2D microscopy image registered within a 3D tomographic image.

The method of registration described above is a part of this propagation process. FIG. 20 shows the result of the registration of a 2D image 2010 to a 3D image 2012. In particular, after undergoing all the translation, rotation, warping and scaling transformations defined in the method, the 2D microscopy thin section 2010 is registered within the sample 2012, to enable coupling of the SEM data from the 2D image 2010 to the 3D data set obtained from the CT image 2012.

Figure 21:
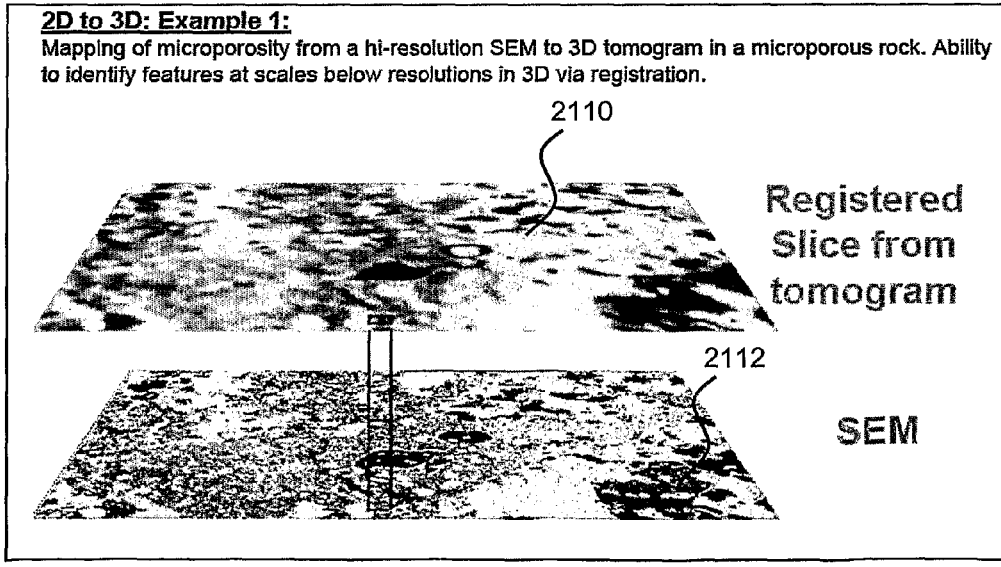
FIG. 21 shows the equivalency of features in two registered images, one of the images being a 2D SEM image and the other image being a corresponding slice from a 3D tomographic image.

An example of registering an image data from a high resolution 2D SEM image to a 3D tomogram of a micro-porous rock sample is shown in FIG. 21. The integrated data obtained from the coupling of microporosity data from the 2D SEM image 2112 onto the 3D tomogram 2110 enables the identification of material features and properties at the resolution of the 2D SEM sample; at higher resolutions than possible via 3D tomography. Generally, tomographic techniques have an inherent resolution limitation (say 1 micron), where microscopy allows one to probe down to scales of nanometers. Thus, an order of up to 1000 times higher resolution is made available by the integration of the two images via image registration. In addition, the large difference in the resolution of the two techniques can be used to measure the true resolution of the 3D image.

Figure 22:
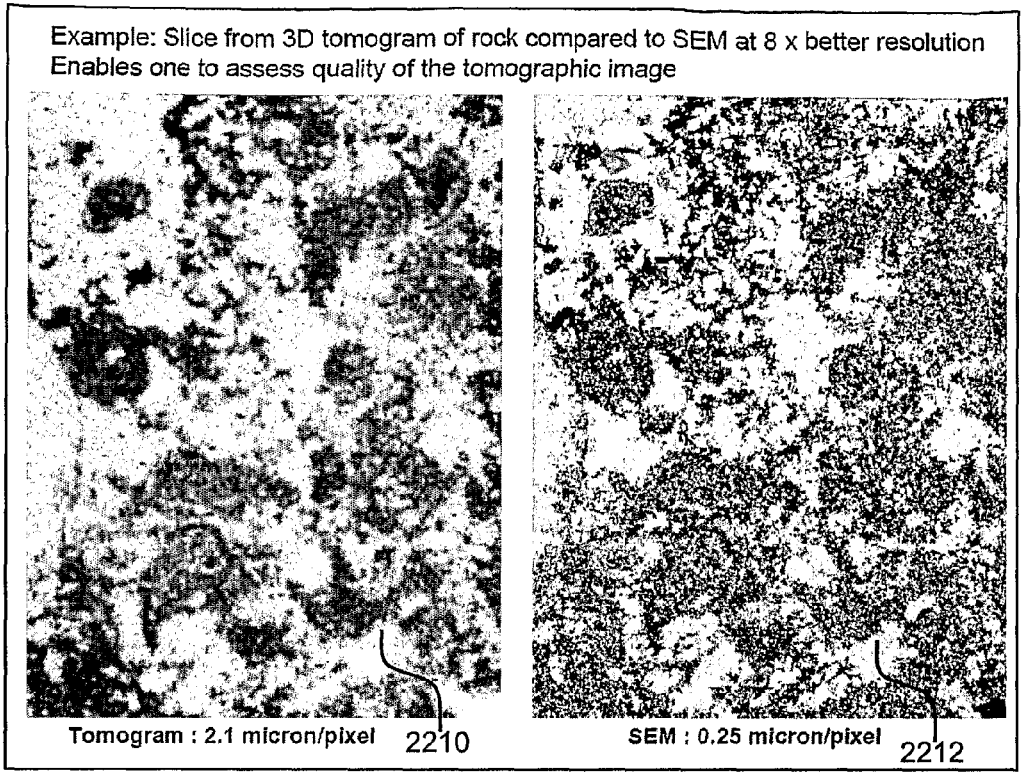
FIG. 22 shows a 2D SEM image and its equivalent slice from a registered 3D tomographic image.
Figure 23:
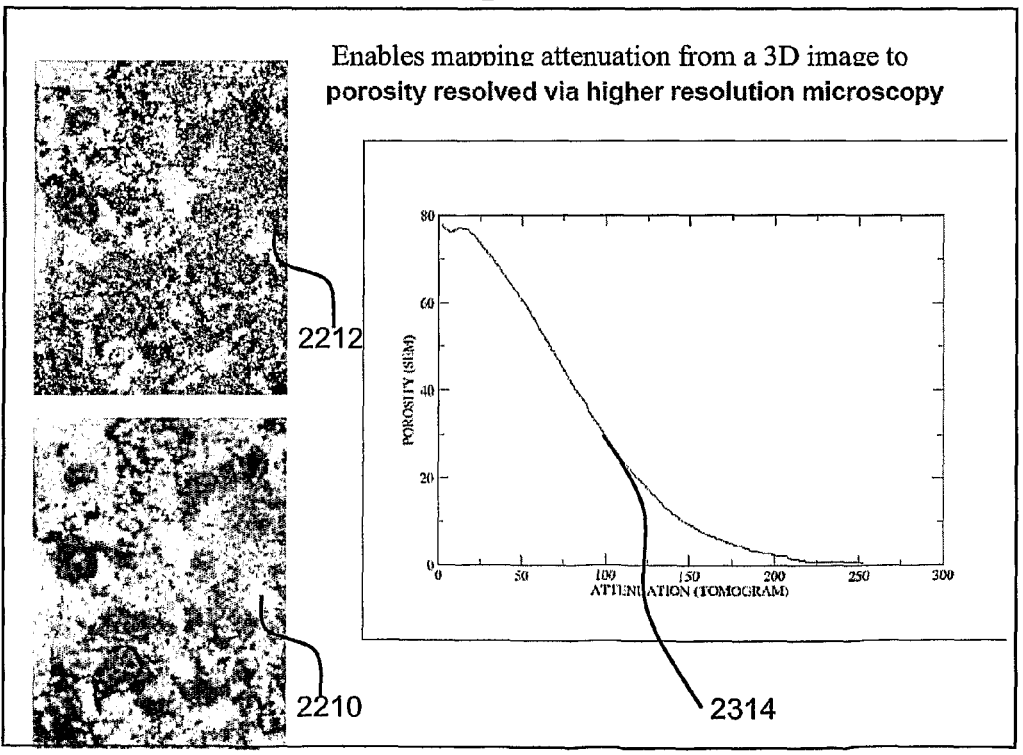
FIG. 23 is a plot of the functional dependence between attenuation data obtained from the 3D tomographic image and porosity data obtained from a 2D microscopy image.

FIG. 22 shows a direct comparison of a 2D slice 2210 from a 3D tomogram of a rock sample with a 2D slice 2212, obtained by SEM. The tomogram 2210 is obtained by way of X-ray CT imaging at 2.1 micron voxel size, while the SEM slice 2212 is obtained at a resolution of 0.25 microns. A quantitative match of the two images 2210 and 2212 is shown in FIG. 23. In particular, FIG. 23 shows a graph that maps the porosity data (associated with the fraction of a particular area that is pore) obtained by a higher resolution 2D image 2212 to the attenuation data obtained from the 3D slice 2210. As seen from the graph 2314, a good correlation between the attenuation and the porosity data is obtained. This enables one to propagate information obtained from the higher resolution 2D microscopy image (in this case the porosity) throughout the entire 3D image. This is based on the attenuation data of the 3D image and using the directly and quantitatively mapped correlation shown by graph 2314.

Other properties obtained at high resolutions from the 2D SEM images can also be quantitatively integrated with registered 3D images. In the example shown in FIGS. 24A and 24B, the SEM image 2410 is obtained at a pixel resolution of 0.25 microns. Image 2414 is a registered slice from an X-ray CT image obtained at a voxel size of 2.5 microns. The X-ray attenuation on this image can be correlated to the pore size data in image 2410. Image 2412 represents mapping of the local pore size distribution on the image data from image 2410; the grey scale in image 2412 corresponds to pore size from 2410. The brighter regions correspond to larger pore sizes.

Figure 24A:
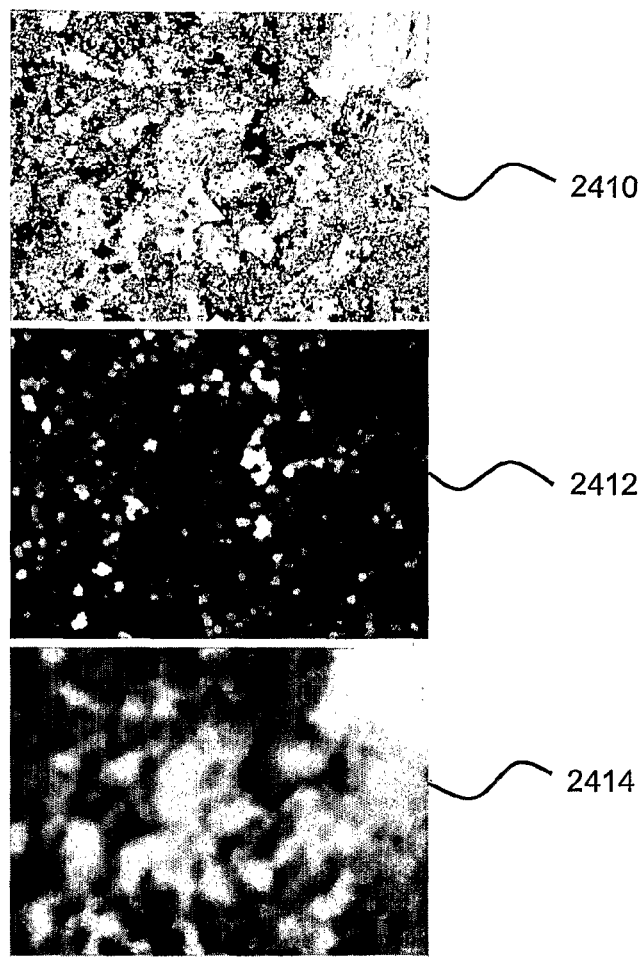
FIG. 24A shows two images of different resolution and an image based on integrated data obtained from the two images.
Figure 24B:
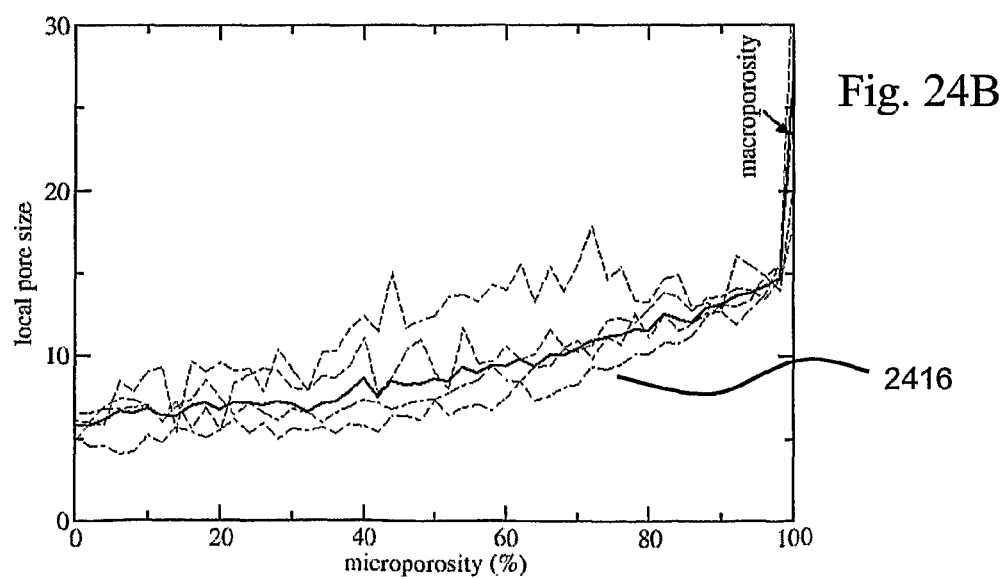
FIG. 24B shows the correlation between the local pore size distribution (y-axis) and the microporosity mapping from the X-ray attenuation (x-axis) plotted on the basis of the image data form the images in FIG. 24A.

FIG. 24B shows a plot of the correlation between the local pore size distribution (y-axis) and the microporosity mapping from the X-ray attenuation (x-axis). This correlation allows mapping the pore sizes throughout the entire 3D image.

Figure 25:
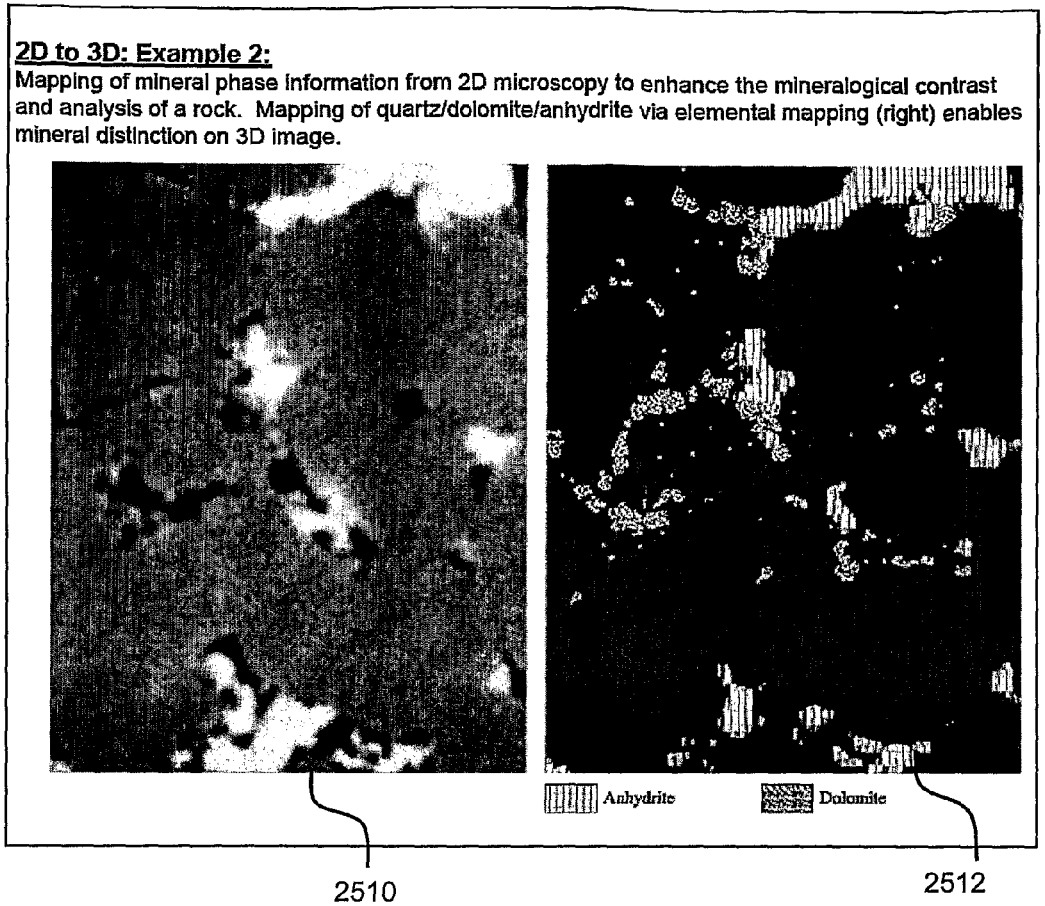
FIG. 25 illustrates mapping mineral phase information from 2D microscopy against attenuation data obtained from a 3D tomographic image.

FIG. 25 illustrates another example of applying quantitative image registration from 2D microscopy to 3D tomography; in this example correlating mineral phase information obtained from elemental mapping (image 2512), to the attenuation data obtained in the registered slice from the 3D image represented by image 2510. The detailed mineral phase distribution shown in the 2D image 2512 indicates the presence of dolomite and anhydrite in the rock sample. These phases are difficult to unambiguously differentiate in the 3D image 2510. By using registration between both images, a quantitative mapping enhances the ability to identify the mineral phase distribution throughout the 3D image.

Further applications will now be described associated with registration of 3D to 3D images. Such registration allows quantitative tracking of changes occurring in a sample after one or more experiments are performed on the sample. A typical application involving 3D to 3D registration usually starts with imaging a sample, which is in a particular state A. After this first image is obtained, the sample is taken away from the imaging setup and various experiments, such as compaction, compression, dissolution, fluid displacement are performed under various conditions. Such experiments lead to changes in the sample state (e.g, micro-structure, mineralogy, fluid saturation). The sample which at this point is in a new state B, is then reintroduced in the imaging system and reimaged. The newly obtained image is then registered with the originally obtained image. The data from the two images may then be integrated and changes that have occurred can be quantified.

The following examples illustrate applications of this method including visualization and quantifying dissolution and particle motion during a set of experiments, imaging of multiple fluid saturation states under varying chemical conditions. An example is also given of alignment of 3D images at multiple scales.

Figure 26:
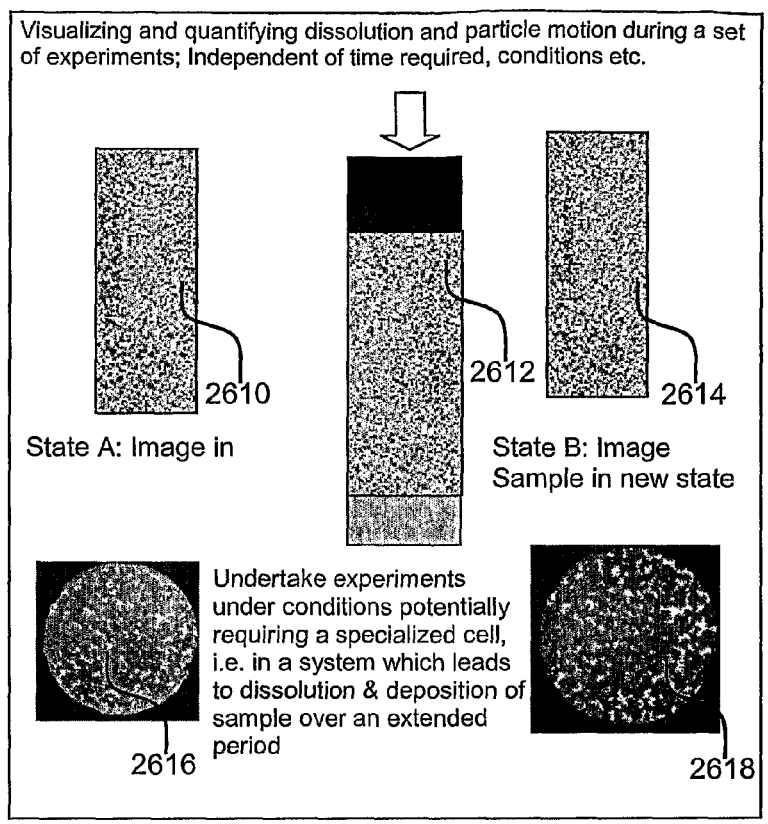
FIGS. 26 and 27 illustrate the concept of taking a 3D image from a sample; conducting an experiment with the sample, wherein the sample is removed from the imaging apparatus; re-imaging the sample and registering the two 3D images obtained before and after the experiment, to identify structural or other changes in the sample.
Figure 27:
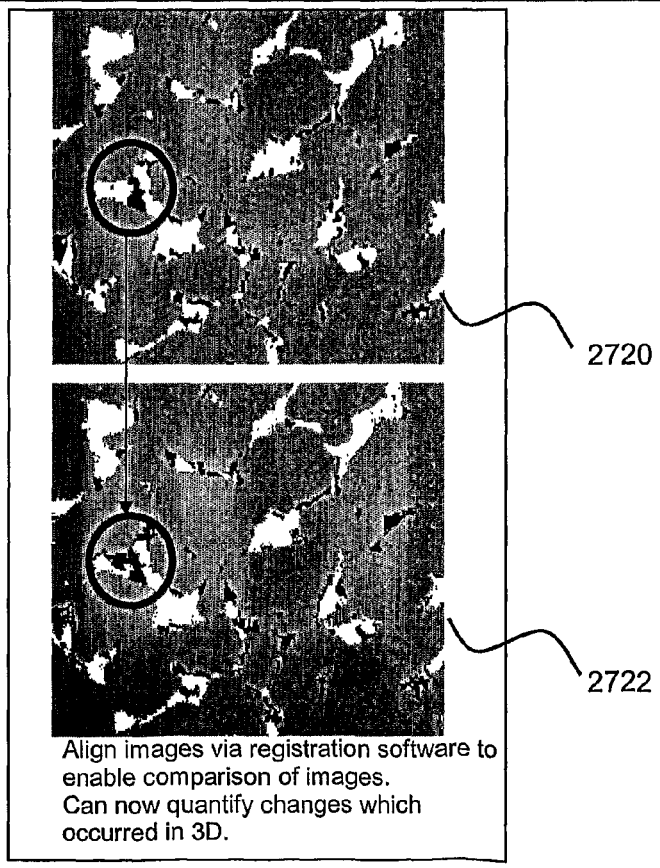

FIGS. 26 and 27 illustrate an experiment of quantitative tracking of changes occurring in the physical structure within a sample volume during a sequence of experiments. Such changes may be mineral specific. A rock sample 2610 is in its original condition, as received in a laboratory. Slice 2616 is from within a 3D image of sample 2610, when the sample is in its original condition. The sample 2610 is then subjected to one or more experiments, as indicated by the intermediate state 2612. In the case of FIG. 26, the sample 2610 was submerged in a fluid of specific composition. The fluid was maintained at an elevated pressure and temperature for a specified period of time. Such conditions, maintained in a specialized cell, can lead to dissolution and deposition of sample material, resulting in changes of the sample microstructure over any extended period. To evaluate any such changes, the sample is reimaged in its new state 2614. A slice 2618 from within the 3D image is also shown in FIG. 26. More detailed insets of 2616 and 2618 are shown in 2720 and 2722 respectively. When comparing slices 2720 and 2722, there are clear visual differences in the sample morphology, caused by the specific experimental conditions. Integrating the two large 3D images associated with slices 2720 and 2722 can result in a number of data sets which capture the microscopic changes which have occurred throughout the sample volume during the transition period. A small subset of examples might include enumerating the change in pore structure, grain structure or fluid permeability which occurred during the transition from 2616 to 2618. These local scale differences/changes can only be identified via the direct registration capabilities included in this method.

Figure 28:
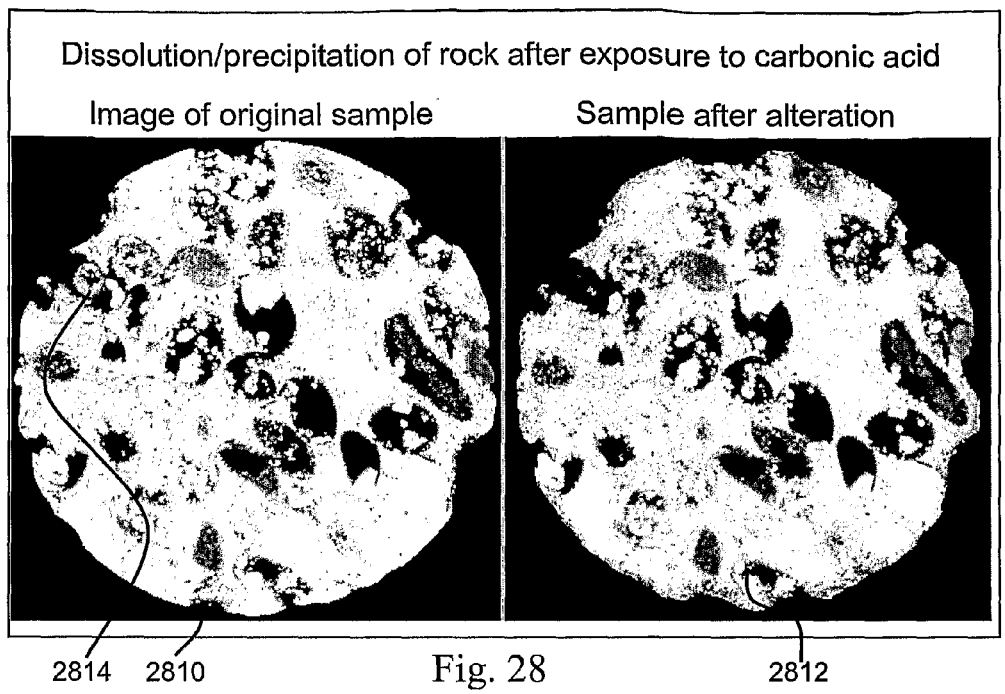
FIG. 28 shows two corresponding slices of registered 3D images of a sample that has been treated with carbonic acid, the obvious structural differences being due to the effect of the acid on the sample material properties.

FIG. 28 shows a different experiment studying the changes in the dissolution/precipitation properties of rock after exposure to carbonic acid. Slice 2810 is a representation of the original 3D image of a rock sample in an initial state. Slice 2812 represents a slice from the registered 3D image taken from the same rock sample after the exposure to carbonic acid over a significant period. By quantitatively registering the two 3D images, before and after the exposure, the resulting morphological changes in the rock sample can be identified. The changes in this particular example are significant and obvious. For example, feature 2814, visible in the original image 2810 has disappeared from the identical, quantitatively registered slice 2812 from the image taken after the acid exposure. Thus, an integrated 3D set of data indicating the differences between the two images allow for changes in the material structure to be quantified (e.g., pore structure, pore shape, grain shapes, microporosity). Changes in physical properties can also be quantified; for example any changes in the flow properties of the sample, due to dissolution and reprecipitation, can be probed using this integrated 3D data set. Further experiments can be conducted under different conditions in order to investigate the consequences of various strategies for dissolution in geological materials.

Figure 29:
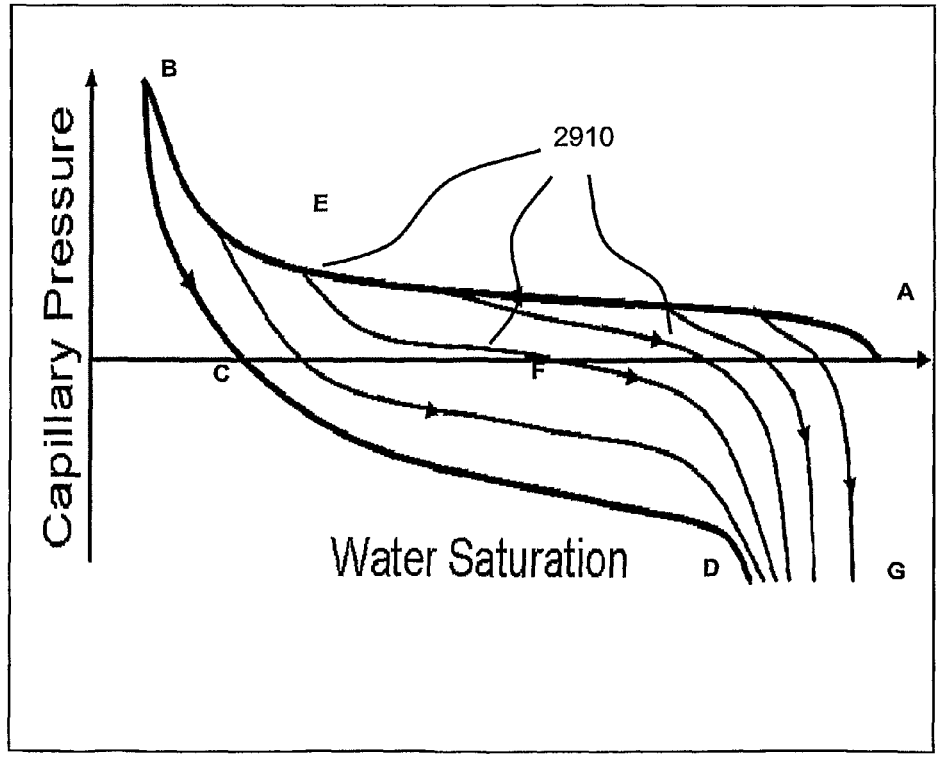
FIG. 29 shows a series of curves defined by sequential states of the sample, each state being characterised by a particular values of water saturation and capillary pressure.

FIG. 29 illustrates a series of curves 2910 formed by various states that occur during the successive flooding (cycling) of oil, gas and/or water through a core sample. Each curve 2910 is an indicative capillary pressure scanning curve for a single wettability state. Image registration enables one to visualize and quantify in 3D the changes which occur in the fluid saturation states during a flooding cycle of a sample (e.g, fluid saturation states after primary drainage, primary spontaneous imbibition, primary forced imbibition, secondary drainage, secondary imbibition, etc.) The graph 2910 identifies various possible paths, such as path A→B→C→D which occurs during a particular series of experiments. A slight variation on this experiment series could result in the path A→E→F→G). The set of experiments might include at least some of the following steps 1. In state A of graph 2910 a rock sample is fully saturated with water.
2. This is followed by oil or gas being injected into the rock to a specified final injection pressure, resulting in states such as B (higher pressure) or E (lower pressure).

3. The oil or gas is then recovered "spontaneously" by letting the system relax while in contact with wetting fluid, yielding states such as C or F respectively.
4. The sample then undergoes a stage of forced wetting fluid injection which may result in either state D or state G.
5. The cycle can be repeated an arbitrary number of times from step 2.

The differences in the fluid structure at each stage in each cycle can be quantified, allowing the relevant multiphase flow properties to be estimated. As stated above, 2910 shows the indicative capillary pressure scanning curve for a single wettability state; the cycles of experiments can be further undertaken on the same core material with other fluids and under different conditions, which will give rise to a different set of capillary pressure/water saturation scanning curves. These states can be in turn imaged and the differences in fluid saturation states imaged and quantitatively compared.

Figure 30:
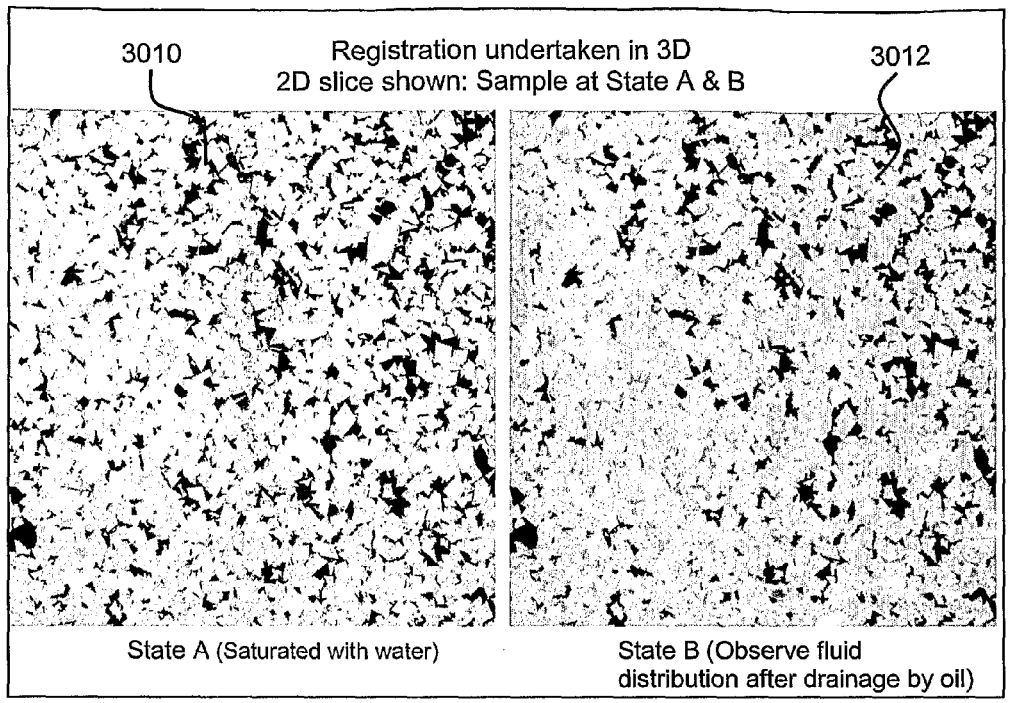
FIGS. 30, 31 and 32A show registered images of samples being in various states with respect to the graph of FIG. 29.
Figure 31:
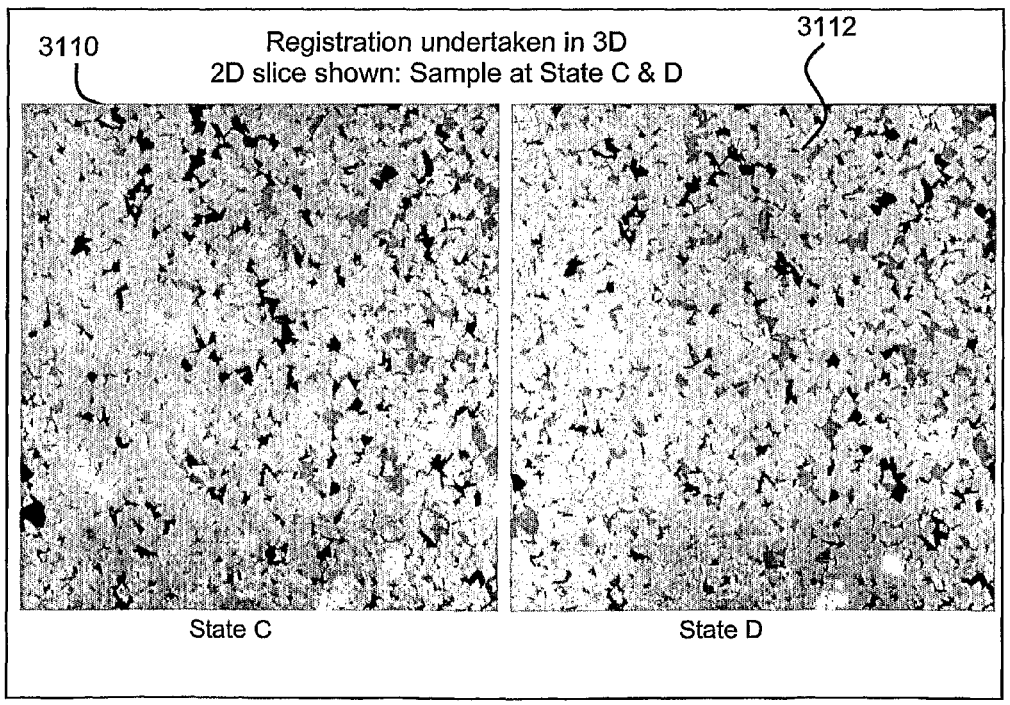

The saturation states shown in FIGS. 30-31 are based on the indicative points A-D on the capillary pressure scanning curve 2910. FIG. 30 shows the change in the fluid distribution between State A, in which the sample is saturated with water 3010 and the same slice from a registered 3D volume in State B, after injection into the sample under pressure with oil (or gas) to connate water saturation 3012. In 3012 the pores where oil has drained into the sample are black and the remaining water saturation is in the smaller (slightly brighter) pores. Quantitative registration allows one to not only identify the amount of fluid injected at State B, which can be measured based on volumetrics, but allows one to directly observe the detailed pore scale distribution of both fluids. The relative flow capacity of the two fluids can be quantified by simulation of the relative permeability of each phase in the 3D image. Such quantitative analysis can produce an estimate of the initial hydrocarbon flow potential of the rock, which can be a parameter of important production implications.

Figure 32A:
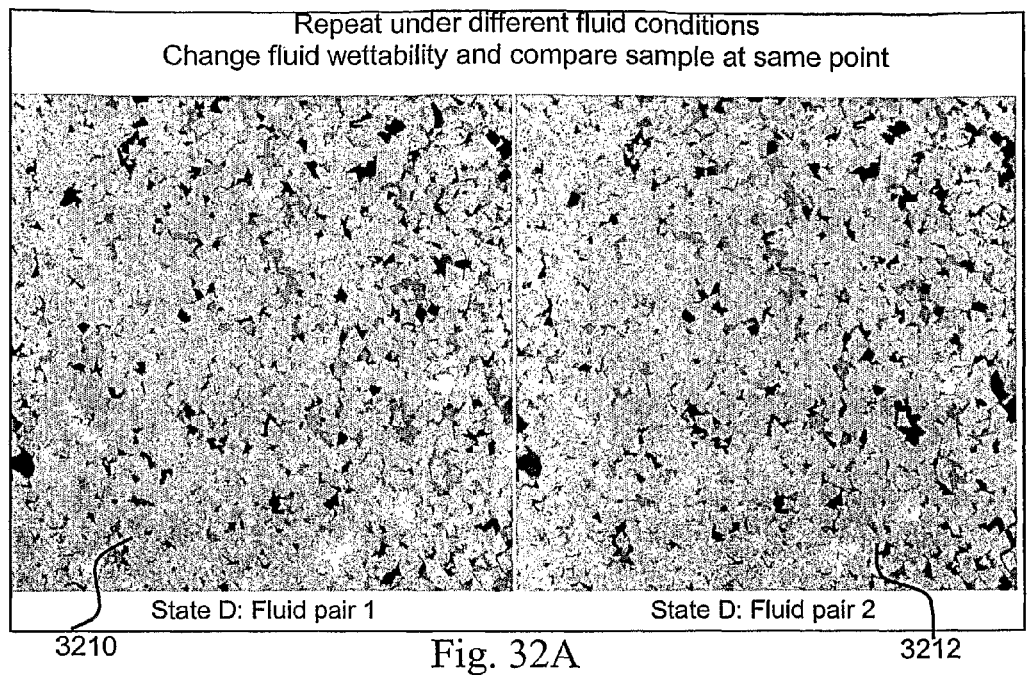
Figure 32B:
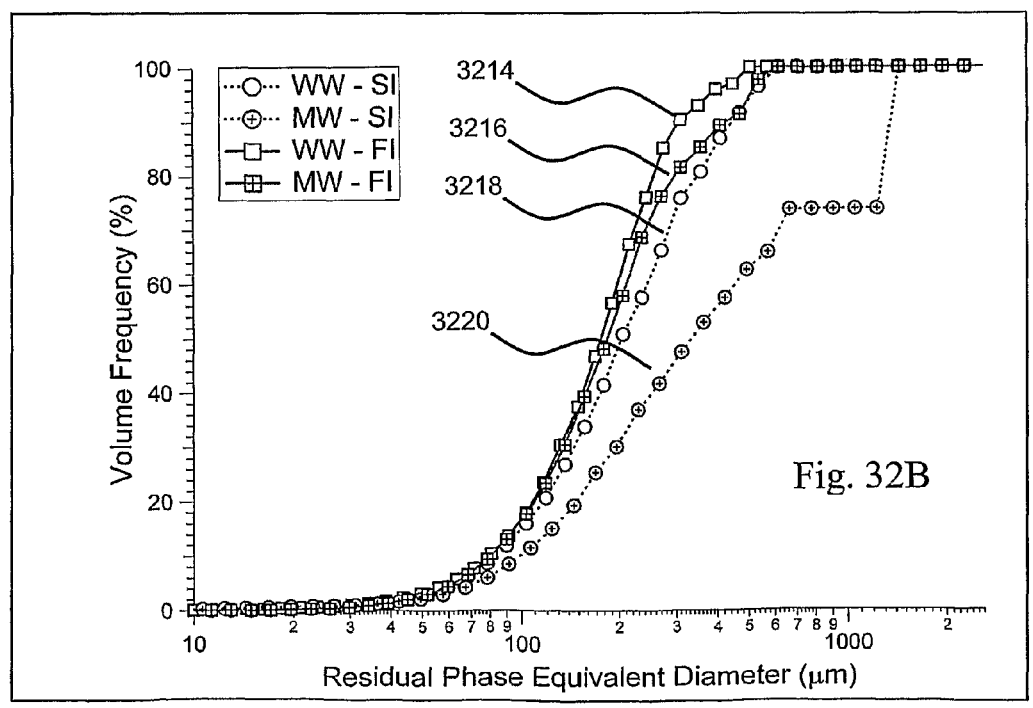
FIG. 32B quantifies the change in the size of the residual hydrocarbon blob size under different wettability conditions.

States C and D in FIGS. 31 and 32A are defined respectively after spontaneous and forced displacement of the oil or gas from the initial (connate water) saturation observed in State B. One can now observe how much oil, or gas, is left in the sample after recovery of oil via both "spontaneous" fluid injection and forced water injection. This observation is very important as it identifies the location of remaining oil and gas. Knowledge of the distribution of the remaining oil or gas in the reservoir will help identify whether it might be considered a candidate for further flooding/treatment as the remaining oil and gas may be moveable by a number of known candidate techniques (e.g., tertiary flooding, low salinity flooding, chemical flooding, injection of surfactant, gas injection, etc.). The movement of the fluids by these techniques can also be directly considered by this method.

FIG. 32A shows the same slice from registered 3D tomograms which illustrate the different resultant residual hydrocarbon distributions obtained after flooding under different wettability conditions—3210 shows the residual hydrocarbon distribution after waterflooding into a water:oil system under water wet conditions and 3212 shows the distribution of the residual hydrocarbon after waterflooding into a water: oil system under mixed wettability (MW) conditions. The distribution of the fluids differs and can be quantified. For example the graphs 3214 to 3220 in FIG. 32B quantify the change in the size of the residual hydrocarbon blob size (important for targeting oil after waterflooding) under these different wettability conditions; in FIG. 32B the size of the residual hydrocarbon blob changes from water wet conditions (graph 3218) to mixed wet conditions (graph 3220) after spontaneous imbibition (SI) and forced imbibition (FI).

FIG. 33 shows how 3D image registration can be used to identify properties of a sample at a number of length scales. Many materials contain 3D structural features of different dimensions (from nanometers to centimeters). One single 3D image cannot capture the full information at all multiple scales (such an image would require 10,000,000 cubed or 200 trillion bytes (200 terabytes). To help bridge the gap needed to probe multiple length scales imaging can be undertaken at multiple scales and quantitative registration used to map fine structure onto the larger domain.

An example is shown in FIG. 33 of an image of a sample which has features that span from the millimeter to nanometer scale. A 3D image represented by the slice 3310 is obtained at a field of view of 4 cm diameter at 20 micron voxel size. This allows features of the material between 20 microns and 4 cm to be discerned. However to probe features at higher resolutions, one or more subsets of the sample originally imaged at the scale of 4 cm have to be reimaged. Image 3312 shows one such example. This image is a subset of the original image 3310 and has been obtained at a resolution of 2.5 microns. Features can now be identified at an improved resolution, which is approximately 8 times better than the original resolution. The information obtained from these two images can be integrated by obtaining a 3D set of imaging data comprising the high resolution image data of image 3312 being mapped against respective voxels of the image 3310.

Figure 34:
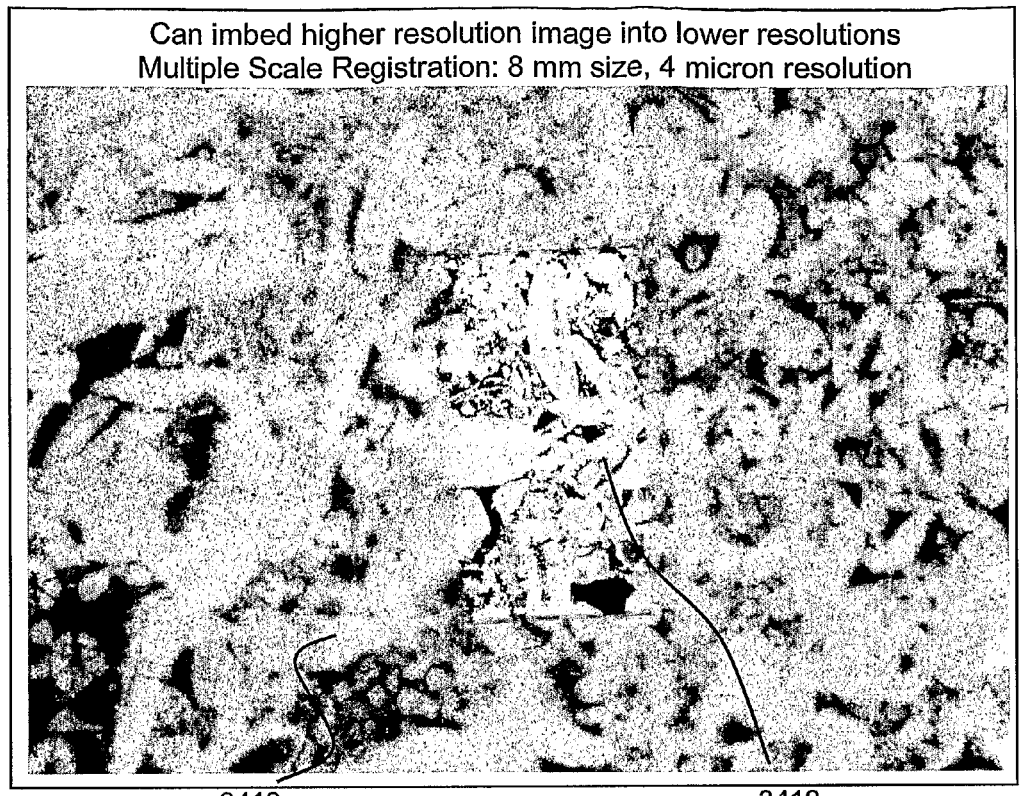
FIG. 34 shows an application of embedding a higher resolution 3D image into a lower resolution 3D image.

FIG. 34 shows the higher resolution image 3412 embedded into the larger image 3410. The higher resolution of image 3412 makes easier identification of features in the image 3410, which otherwise may become difficult to "resolve" after numerous reproductions.

Figure 35:
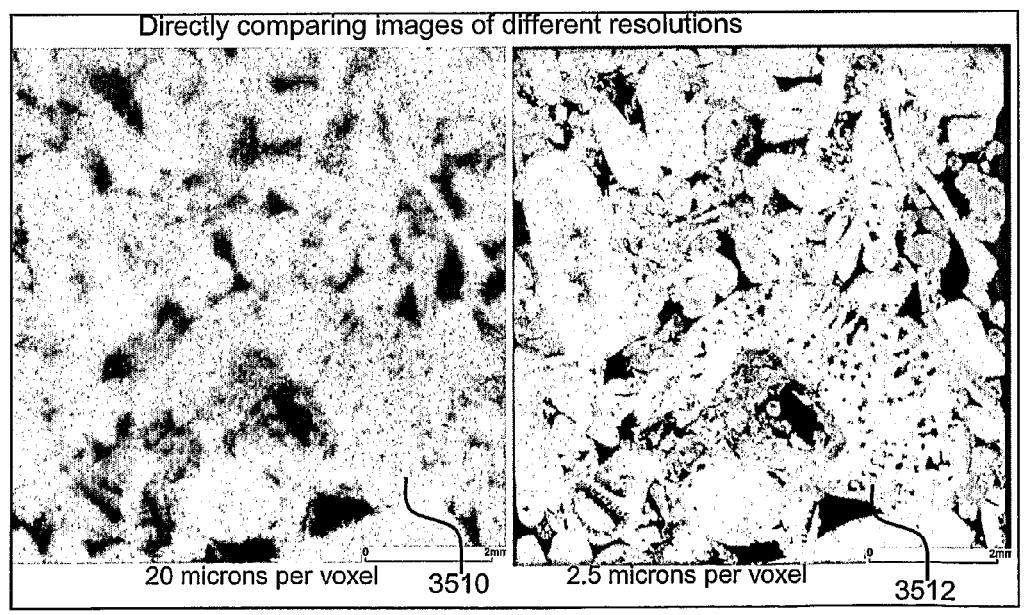
FIG. 35 shows corresponding slices from registered 3D images of different resolution arranged for direct comparison.

FIG. 35 shows a side by side comparison of the same sub-region of images with different resolutions. Feature not resolved at the lower resolution image 3510 can now be identified in the higher resolution image 3512. Due to the exact and quantitative nature of the image registration, one can use features identified at the higher resolution image to "populate" poorly or unresolved features in the larger image. Grey scales identified in the image 2510 can be directly mapped to phases clearly identified in the higher definition image 3512. For example porosity and pore sizes clearly observed in the image 3512 can be correlated to the grey scale values identified in the left hand image. Analogous to the propagation/integration of 2D data into a 3D volume shown in FIGS. 23 and 24, relevant 3D structural information (e.g., pore size, pore shape, grain structure) from 3412 and 3512 can be propagated through the image data at larger volumes (3410 and 3510 respectively)

F. Other Aspects

The disclosed method and the system facilitate coupling the detailed structural information available from conventional microscopic techniques (both mineralogy and probing submicron scales) to 3D X-ray micro-CT data. In particular, the disclosed methodology allows an optimal registration of detailed 2D microscopy images onto 3D images obtained from micro-CT. This result greatly extends the capabilities of conventional micro-CT imaging.

In addition, a methodology and a system are disclosed that measure the 3D pore scale distribution of fluids on the same 3D porous sample under a variety of wettability conditions and saturation states. The method allows removing the porous sample from the beamline, undertaking a set of experiments on the system in the laboratory, and re-imaging the sample at a later date to obtain voxel to voxel registration of the 3D images.

It is apparent from the above description that, as a result of the application of the disclosed method for processing image data, integrated image data is obtained that comprises information about one or more characteristics of the sample. The obtained information is additional to that available from each individual image. Furthermore, since the information can be extrapolated beyond the regions of overlap between the images, the method enables information to be obtained that is additional to the combined information available from the original images that take part in the registration process.

Furthermore, the method allows an estimate to be made of the spatial distribution of a characteristic of the sample throughout the imaged region of the sample, and even throughout the entire sample. Here the expression "characteristic" has been used in very broad term and is intended to encompass any feature or property comprising information of the sample. Examples of such characteristic may comprise at least one of the following; physical properties, structural properties, chemical properties, mineralogy, porosity, permeability, acoustic properties, grain size, pore size, elastic properties, surface properties and local surface interaction, connectivity characteristics, grain boundaries, cementing phases, geofacies types and geological rock type, mineral phase structure or pore fluid distribution of the sample. Notably, this advantageous capability of the disclosed method is also applicable in the case of registration of processing of two 3D images.

It is apparent from the above examples that the described arrangements are applicable to gas, oil and mining industries. However, it is envisaged that the described techniques can also be applied in other industries.

While the above description has been directed to methods for registering and integrating 2D and 3D images, it should be noted that other applications are also considered within the scope of this invention. For example, the invention is also related to one or more respective computer systems, including memory and one or more microprocessors programmed to perform the computational routine effecting the registering and integrating of data from the 2D/3D images and from the 3D/3D images. The computation process can be performed by using at least one of the task parallelism and data parallelism discussed in the workflow section. A computer program and computer product including computer readable medium comprising a computer program, that is executable to perform the described methods, is also within the scope of the invention.

In addition, it has to be noted that, while the described methods are associated with micro-CT, other methods for 3D imaging can also be used to obtain the 3D images processed by the described methods such as, but not limited to MRI, confocal microscopy, ultrasound, SPECT and PET.

The invention claimed is:

1. An image data processing method comprising:
   registering a first set of 3D image data and a second set of 3D image data of at least partially overlapping spatial regions of a porous sample material to achieve voxel alignment, said first set of 3D image data corresponding to a dry sample of said sample material and said second set of 3D image data corresponding to a fluid saturated sample of said sample material; and
   processing said registered image data to obtain integrated image data by superposition of voxels of said first set of 3D image data with correspondingly registered voxels of the second set of 3D data image to obtain a quantitative estimate of the spatial distribution of a property of the sample material not available from said first set of 3D image data and said second set of 3D image data alone.

2. The method of claim 1, wherein said registering is performed by an iterative spatial transformation algorithm using a quality metric.

3. An image data processing apparatus comprising:
   a memory storing a first set of 3D image data and a second set of 3D image data of at least partially overlapping spatial regions of a sample material, said first set of 3D image data corresponding to a dry sample of said sample material and said second set of 3D image data corresponding to a fluid saturated sample of said sample material; and
   a processing circuit configured to register said first set of 3D image data and said second set of 3D image data to achieve voxel alignment, and process said registered image data to obtain integrated image data by superposition of voxels of said first set of 3D image data with correspondingly registered voxels of the second set of 3D image data to obtain a quantitative estimate of the spatial distribution of a property of the sample material not available from said first set of 3D image data and said second set of 3D image data alone.

4. The apparatus of claim 3, wherein said processing circuit performs said registering by an iterative spatial transformation algorithm and quality metric.

5. The apparatus of claim 3, wherein said processing circuit comprises at least two processors configured to perform said registration and processing as a parallel task and/or parallel data workflow.

6. A computer program product comprising a non-transitory computer useable medium including a computer readable program, wherein the computer readable program, when executed on a computer, causes the computer to:
   register a first set of 3D image data and a second set of 3D image data of at least partially overlapping spatial regions of a porous sample material to achieve voxel alignment, said first set of 3D image data corresponding to a dry sample of said sample material and said second set of 3D image data corresponding to a fluid saturated sample of said sample material; and
   process said registered image data to obtain integrated image data by superposition of voxels of said first set of 3D image data with correspondingly registered voxels of the second set of 3D image data to obtain a quantitative estimate of the spatial distribution of a property of the sample material not available from said first set of 3D image data and said second set of 3D image data alone.

* * * * *